United States Patent
Singleton et al.

(10) Patent No.: US 12,254,971 B2
(45) Date of Patent: Mar. 18, 2025

(54) LOCATION-BASED ACTIVITY TRACKING

(71) Applicant: Oura Health Oy, Oulu (FI)

(72) Inventors: Alec Singleton, Toronto (CA); Janne Kukka, Santa Barbara, CA (US); Jukka Partanen, Mäntsälä (FI); Dmitry Sergeev, Helsinki (FI); Azeem Akhter, Helsinki (FI)

(73) Assignee: Oura Health Oy, Oulu (FI)

( * ) Notice: Subject to any disclaimer, the term of this patent is extended or adjusted under 35 U.S.C. 154(b) by 211 days.

(21) Appl. No.: 17/410,858

(22) Filed: Aug. 24, 2021

(65) Prior Publication Data

US 2023/0065695 A1    Mar. 2, 2023

(51) Int. Cl.
*G16H 20/30* (2018.01)
*G06F 1/16* (2006.01)
*G06F 9/451* (2018.01)

(52) U.S. Cl.
CPC ............. *G16H 20/30* (2018.01); *G06F 1/163* (2013.01); *G06F 9/451* (2018.02)

(58) Field of Classification Search
CPC .......... G16H 20/30; G06F 9/451; G06F 1/163
See application file for complete search history.

(56) References Cited

U.S. PATENT DOCUMENTS

| | | | |
|---|---|---|---|
| 9,582,034 B2 | 2/2017 | von Badinski et al. | |
| 9,950,236 B1* | 4/2018 | Jooste | A63B 71/06 |
| 10,488,527 B2 | 11/2019 | Venkatraman et al. | |
| 10,953,307 B2* | 3/2021 | Wilson | A61B 5/1112 |
| 11,806,109 B2 | 11/2023 | Yuen et al. | |
| 2007/0011919 A1* | 1/2007 | Case | A43B 1/0036 36/132 |
| 2008/0165017 A1* | 7/2008 | Schwartz | A61B 5/486 600/324 |
| 2015/0258415 A1* | 9/2015 | Trivedi | G09B 19/0038 700/91 |
| 2016/0166161 A1* | 6/2016 | Yang | A61B 5/02438 600/476 |
| 2016/0263435 A1* | 9/2016 | Venkatraman | A61B 5/1123 |
| 2016/0345891 A1* | 12/2016 | Kirby | A43B 13/181 |
| 2017/0039480 A1* | 2/2017 | Bitran | A61B 5/01 |
| 2018/0043210 A1* | 2/2018 | Niehaus | A61B 5/1118 |
| 2020/0237317 A1 | 7/2020 | Newberry et al. | |

(Continued)

OTHER PUBLICATIONS

Xu, J. Y. (2015). Personalized, quantifiable, multi-layered daily life profiling for wireless health: Methodologies and systems (Order No. 3680880). Available from ProQuest Dissertations and Theses Professional. (Year: 2015).*

*Primary Examiner* — Matthew L Hamilton
(74) *Attorney, Agent, or Firm* — Holland & Hart LLP

(57) ABSTRACT

Methods, systems, and devices for activity tracking are described. A method for automatic activity detection may include receiving physiological data associated with a user from a wearable device and identifying an activity segment during which the user is engaged in a physical activity based on the physiological data. The method may further include identifying location data associated with the user for at least a portion of the activity segment and identifying one or more parameters associated with the physical activity based on the physiological data and the location data. The method may further include causing a user device to display the one or more parameters associated with the physical activity.

20 Claims, 10 Drawing Sheets

(56) References Cited

U.S. PATENT DOCUMENTS

| | | | |
|---|---|---|---|
| 2021/0068713 A1* | 3/2021 | Dervisoglu | A61B 5/0205 |
| 2021/0093917 A1* | 4/2021 | Dervisoglu | A63B 24/0062 |
| 2021/0093918 A1* | 4/2021 | Dervisoglu | H04W 4/021 |
| 2021/0169417 A1* | 6/2021 | Burton | A61B 5/4857 |
| 2021/0170232 A1* | 6/2021 | Kabbash | A63B 24/0062 |
| 2021/0341300 A1* | 11/2021 | Beaurepaire | G01C 21/3492 |
| 2022/0093256 A1* | 3/2022 | Keith, Jr. | G06F 21/316 |
| 2023/0148910 A1* | 5/2023 | Hu | A63B 24/0062 482/9 |
| 2023/0285808 A1* | 9/2023 | Jeong | G16H 20/30 |

\* cited by examiner

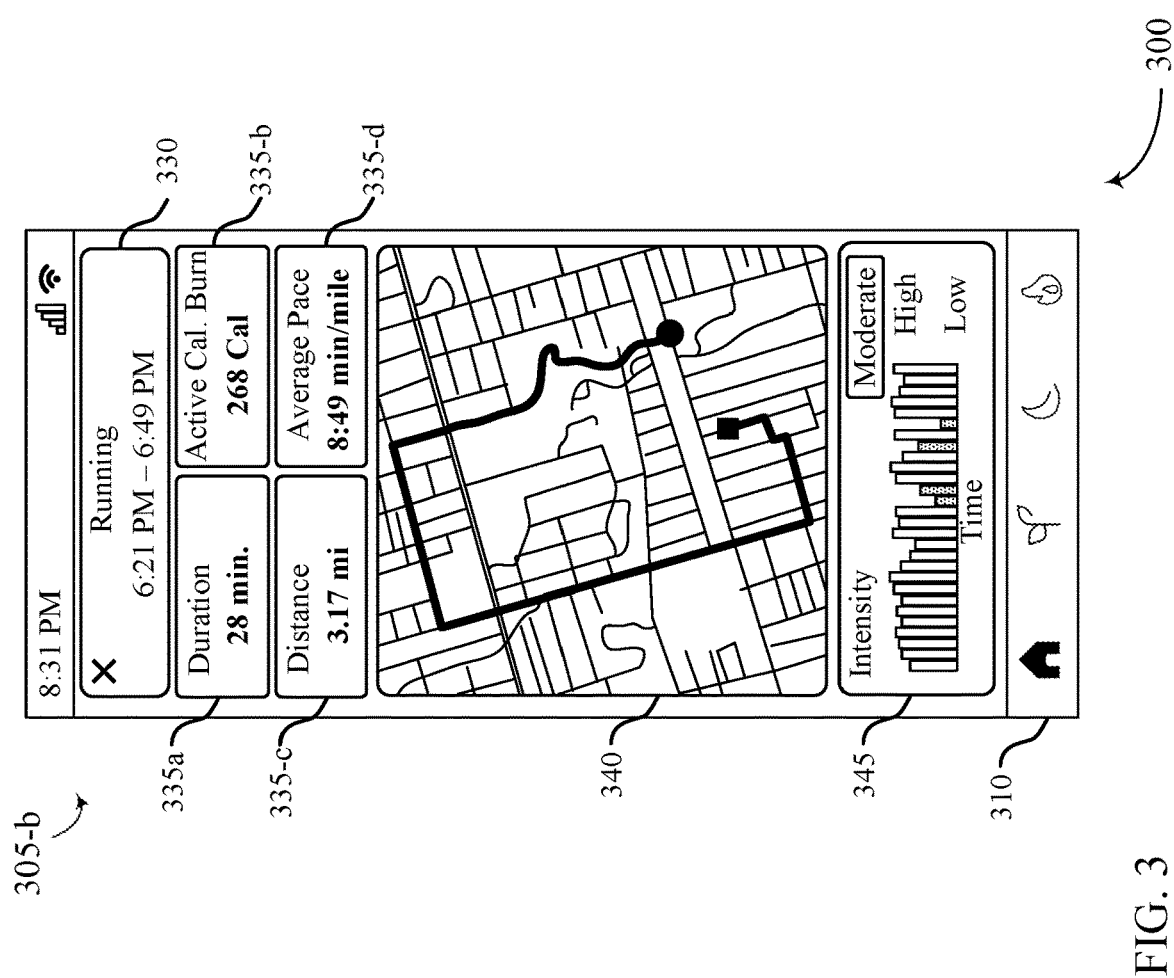
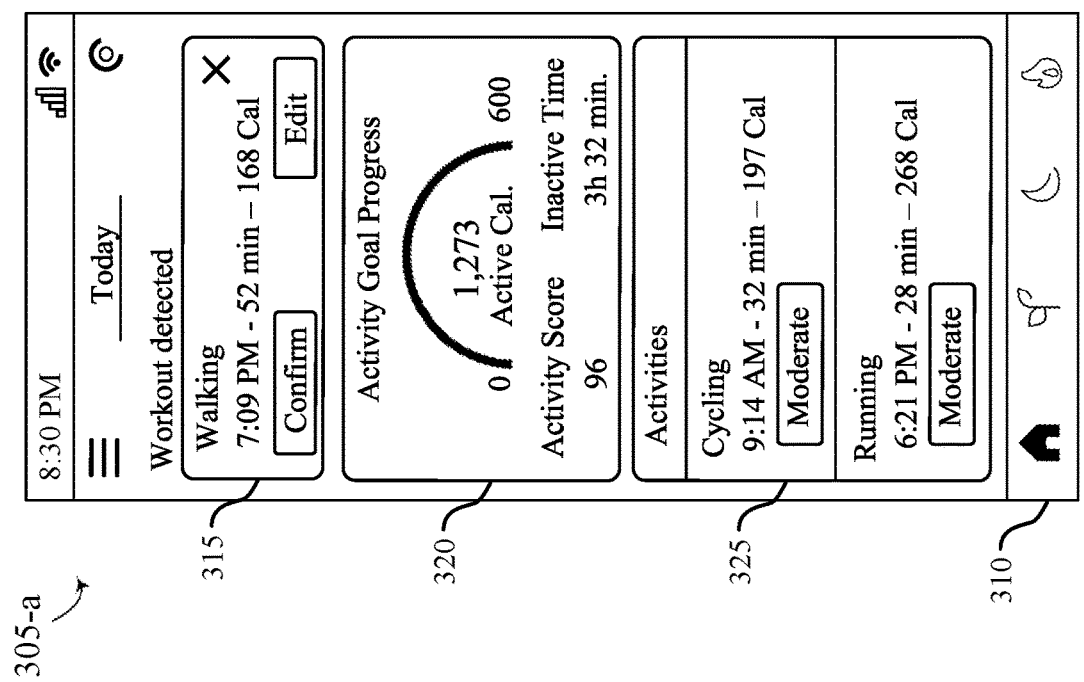
FIG. 3

LOCATION-BASED ACTIVITY TRACKING

FIELD OF TECHNOLOGY

The following relates to wearable devices and data processing, including location-based activity tracking.

BACKGROUND

Some wearable devices may be configured to collect data from users associated with movement and other activities. For example, some wearable devices may be configured to detect when a user is engaged in physical activity. However, conventional activity tracking techniques implemented by some wearable devices are deficient.

BRIEF DESCRIPTION OF THE DRAWINGS

FIG. 3 illustrates an example of a graphical user interface (GUI) that supports techniques for location-based activity tracking in accordance with aspects of the present disclosure.

DETAILED DESCRIPTION

Figure 1:
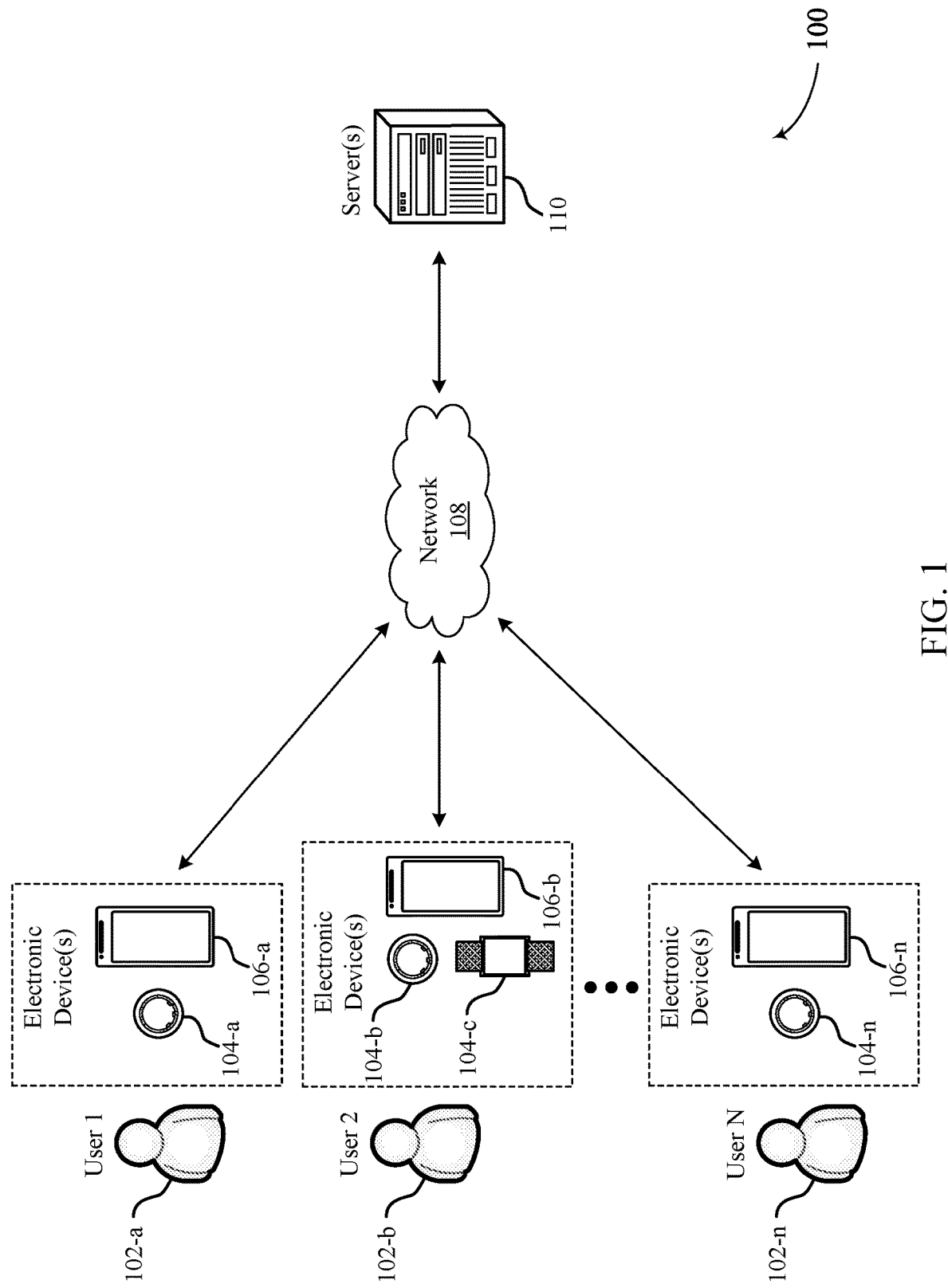
FIG. 1 illustrates an example of a system that supports techniques for location-based activity tracking in accordance with aspects of the present disclosure.

Some wearable devices may be configured to collect data from users associated with movement and other activities. For example, some wearable devices may be configured to detect when a user is engaged in physical activity and predict the type of physical activity based on measured physiological data, motion data, or both. Such activity tracking devices may detect that the user is engaged in a physical activity after the physiological data or motion data satisfies a threshold and may prompt the user to confirm whether they are engaged in the predicted physical activity. These activity tracking devices may only calculate parameters or characteristics for an identified activity from the time the user confirms the respective activity. Such techniques may lead to inaccurate activity tracking, as they may omit or otherwise disregard physical activity which occurred prior to confirmation of the activity segment. Similarly, such activity tracking devices may prompt a user to confirm completion of a physical activity after detecting physiological data or motion data that indicates the user is no longer engaged in the activity, which may lead to the activity tracking device inaccurately calculating or including characteristics for the activity even after the user has ended the activity.

According to some aspects of the present disclosure, techniques described herein may leverage location information in order to more efficiently and accurately perform activity tracking such as predicting when an activity has started and stopped. In particular, techniques described herein may utilize both physiological data collected from a user via a wearable device along with location information for the user to identify periods of time during which the user is engaged in physical activity, and parameters or characteristics associated with the identified physical activity (e.g., speed, pace, distance, route map, elevation gain).

According to some aspects of the present disclosure, physiological data collected from a user via a wearable device may be used to identify time intervals during which the user is engaged in physical activity (e.g., "activity segments"). In some cases, a system may automatically identify that the user is engaged in physical activity (e.g., without input from the user). Additionally, or alternatively, a system may prompt a user to confirm whether they are (or were) engaged in physical activity, and may identify an activity segment based on a confirmation received from the user. Similarly, in some aspects, the system may automatically detect a completion of an identified activity segment (e.g., without input from the user), based on a confirmation of a completion of the activity segment received from the user, or both. In some aspects, the system may classify an identified activity segment as corresponding to one or more activity types (e.g., running, walking, cycling). Each activity type may be associated with a corresponding confidence value, and may be confirmed or edited by the user. In some implementations, the system may utilize location data (e.g., Global Positioning System (GPS) data) associated with the user in order to more accurately determine parameters associated with an identified activity segment (e.g., start time, stop time, start location, stop location, speed, route, distance, etc.). In some aspects, location data may be determined from data generated or collected via a user device corresponding to each given user and/or each given wearable device. Location data may be used to determine one or more parameters associated with an identified activity segment or physical activity. For example, in cases where a system detects that a user went for a run (e.g., running activity segment), location data for the user may be used to determine start/end points for the run, a duration of the run, a route map for the run, and the like. In some implementations, techniques described herein may perform continuous location tracking. Deriving locations (e.g., starting position, ending position) using continuous location data may be much more accurate as compared to some conventional solutions, as it may enable systems and methods described herein to retroactively pinpoint when and where an activity (e.g., exercise) happened. This may enable more efficient activity detection (e.g., identify start/stop of an activity segment to within one minute, as compared ten minutes for some other solutions). Moreover, location data may be used to determine an elevation change for the run, a pace, an elevation-adjusted pace, and the like. In this regard, leveraging location data along with physiological data collected from a wearable device may be used to improve activity tracking for a user.

Aspects of the disclosure are initially described in the context of systems supporting physiological data collection from users via wearable devices. Additional aspects of the disclosure are described in the context of example graphical user interfaces (GUIs) for location-based activity tracking.

Aspects of the disclosure are further illustrated by and described with reference to apparatus diagrams, system diagrams, and flowcharts that relate to location-based activity tracking.

FIG. 1 illustrates an example of a system 100 that supports techniques for location-based activity tracking in accordance with aspects of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like). 15

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices which utilize LEDs which are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time during which the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as sleep scores, readiness scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight." or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices/components of the system 100 may support techniques for location-based activity tracking. In particular, the system 100 illustrated in FIG. 1 may support techniques for identifying when a user 102 is engaged in a physical activity based on physiological data collected via a wearable device 104 (e.g., ring 104), and utilizing location data for the user 102 to determine one or more parameters for the detected physical activity.

For example, as shown in FIG. 1, the ring 104-*a* may collect physiological data from the user 102-*a* (e.g., User 1), including temperature data, heart rate data, accelerometer data, respiratory rate data, and the like. The physiological data collected by the ring 104-*a* may be used to determine periods of time (e.g., "activity segments") during which the user 102-*a* is engaged in physical activity. For example, the system 100 may determine that the user 102-*a* exhibits heightened temperature readings, heightened heart rate, and heightened respiratory rate, and may therefore determine that the user 102-*a* is engaged in a physical activity. Identification of an activity segment (e.g., time interval during which the user 102-*a* is engaged in physical activity) may be performed by any of the components of the system 100, including the ring 104-*a*, the user device 106-*a*, the servers 110, or any combination thereof.

In some cases, the system 100 may automatically identify that the user 102-*a* is engaged in physical activity without input from the user 102-*a*. For example, the system 100 may identify an activity segment for the user 102-*a* based on physiological data collected via the ring 104-*a*, and without receiving any user input from the user 102-*a*. Additionally, or alternatively, the system 100 may prompt the user 102-*a* to confirm whether they are (or were) engaged in physical activity, and may identify an activity segment based on a confirmation received from the user 102-*a* (e.g., via a user input received via the user device 106-*a*). Similarly, in some aspects, the system 100 may automatically detect a completion of an identified activity segment without input from the user 102-*a*. For example, in some cases, the system 100 may identify that the user's temperature and heart rate are both lowering, and may therefore automatically identify a completion of the activity segment. In other words, the system 100 may utilize physiological data collected from the ring 104-*a* (and/or location data) to automatically determine that the user 102-*a* is no longer engaged in a physical activity.

Continuing with the same example, in some implementations, the system 100 may utilize location data (e.g., GPS data) associated with respective users 102 in order to more accurately determine parameters associated with an identified activity segment. In some aspects, location data for each respective user 102 may be generated, received, or otherwise acquired via a corresponding user device 106, ring 104, or other wearable device 104. For example, in cases where the user device 106-*a* is enabled with GPS capabilities, location data for the first user 102-*a* may be determined based on data generated/received via the user device 106-*a*. Additionally, or alternatively, the ring 104-*a* may be enabled with GPS or other positioning capabilities. By way of another example, in cases where the wearable device 104-*c* (e.g., watch 104-*c*) is enabled with GPS capabilities, location data for the second user 102-*b* may be determined based on data generated/received via the wearable device 104-*c*.

Location data may be used to determine one or more parameters associated with an identified activity segment or physical activity. For example, in cases where the system 100 detects that the user 102-*a* went for a run (e.g., running activity segment), location data for the user 102-*a* may be used to determine start/end points for the run, a duration of the run, a route map for the run, and the like. Moreover, location data may be used to determine an elevation change for the run, a pace, an elevation-adjusted pace, calories burned, and the like. In this regard, leveraging location data along with physiological data collected via the ring 104-*a* may be used to improve activity tracking for the user 102-*a*.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
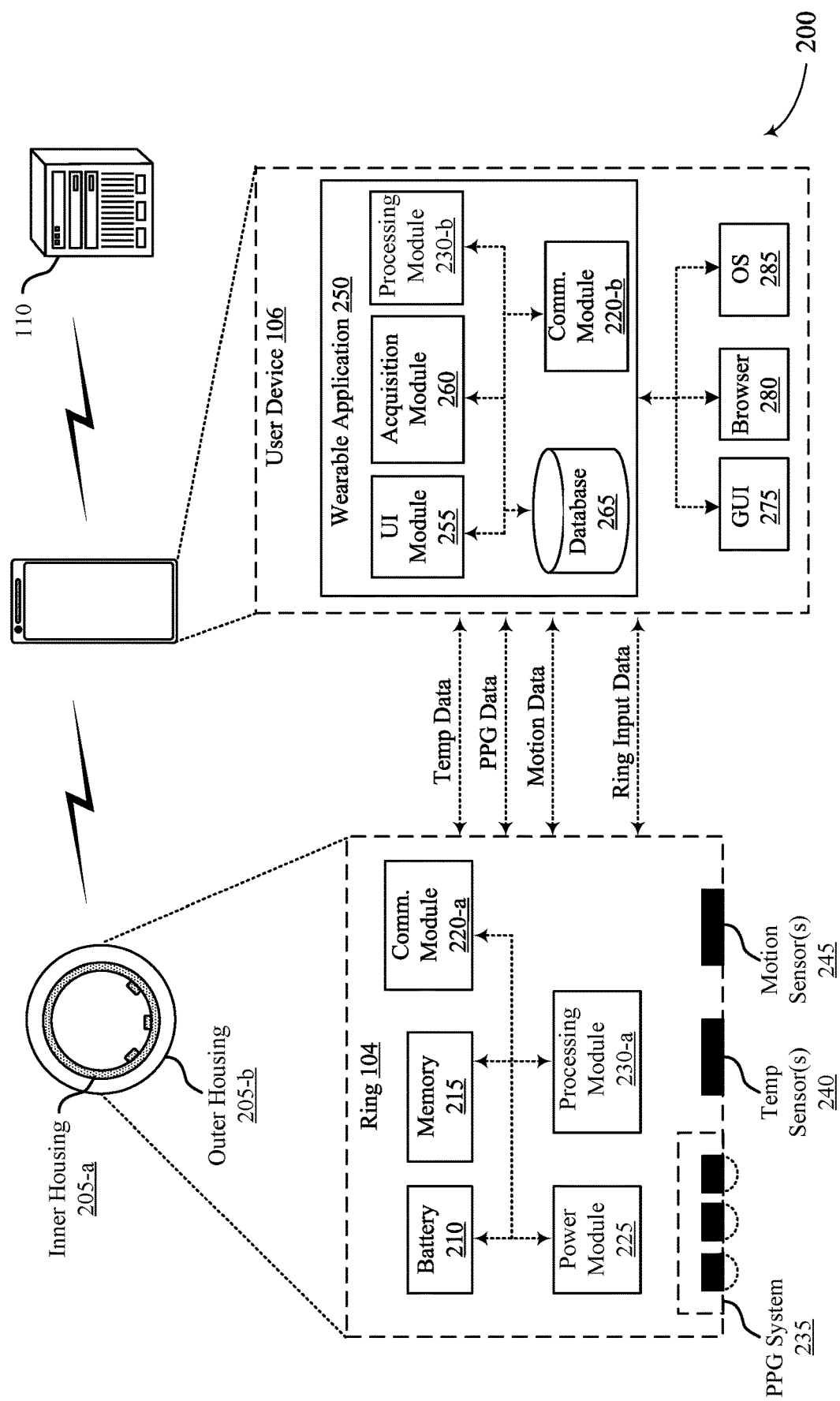
FIG. 2 illustrates an example of a system that supports techniques for location-based activity tracking in accordance with aspects of the present disclosure.

FIG. 2 illustrates an example of a system 200 that supports techniques for location-based activity tracking in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI 160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a sleep score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations which require relatively low processing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., sleep score, readiness score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, sleep scores, readiness scores, and the like.

In some cases, "sleep days" may align with the traditional calendar days, such that a given sleep day runs from midnight to midnight of the respective calendar day. In other cases, sleep days may be offset relative to calendar days. For example, sleep day's may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., sleep score, readiness score) may be determined/calculated based on one or more "contributors," "factors," or "contributing factors." For example, a user's overall sleep score may be calculated based on a set of contributors, including: total sleep, efficiency, restfulness, REM sleep, deep sleep, latency, timing, or any combination thereof. The sleep score may include any quantity of contributors. The "total sleep" contributor may refer to the sum of all sleep periods of the sleep day. The "efficiency." contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall readiness score may be calculated based on a set of contributors, including: sleep, sleep balance, heart rate, HRV balance, recovery index, temperature, activity, activity balance, or any combination thereof. The readiness score may include any quantity of contributors. The "sleep" contributor may refer to the combined sleep score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the readiness score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the respective devices of the system 200 (e.g., ring 104, user device 106, servers 110) may support techniques for location-based activity tracking. In particular, the system 200 illustrated in FIG. 2 may support techniques for identifying when a user 102 is engaged in a physical activity based on physiological data collected via the ring 104, and utilizing location data for the user 102 to determine one or more parameters/characteristics for the detected physical activity. In some aspects, detected activity segments for the user (e.g., detected time intervals during which the user was engaged in physical activity) may be used to update respective scores for the user, such as activity scores, readiness scores, and the like.

For example, as shown in FIG. 2, the ring 104 may collect physiological data from a user 102, including temperature data, heart rate data, and the like. The physiological data collected by the ring 104 may be used to determine periods of time (e.g., "activity segments") during which the user 102 is engaged in physical activity. In other words, the system 200 may identify activity segments for the user (e.g., time intervals during which the user is engaged in physical activity) based on the received physiological data. For example, the system 200 may determine that the user exhibits heightened temperature readings, heightened heart rate, and heightened respiratory rate, and may therefore determine that the user 102 is engaged in a physical activity (e.g., identify an activity segment for the user). Further, the system 200 may be configured to search through collected location data to determine the exact starting and ending positions/locations of the identified activity segment.

In some aspects, the system 200 may be configured to train one or more algorithms or classifiers (e.g., machine learning classifiers, neural networks, machine learning algorithms) to identify activity segments. For example, acquired physiological data may be input into a machine learning classifier to train the machine learning classifier to identify activity segments for the user. In some aspects, classifiers may be trained for each respective user such that the classifiers are "tailored" to identify activity segments based on the user's own unique physiological characteristics.

It is noted herein that the various processes and operations described herein may be performed by any of the components of the system 200. For example, identification of activity segments may be performed by any of the components of the system 200, including the ring 104, the user device 106, the servers 110, or any combination thereof. For instance, physiological data collected by the ring 104 may be transmitted to the user device 106, where the user device 106 forwards or relays the physiological data to the servers 110 for identification of activity segments.

In some implementations, the system 200 may utilize location data (e.g., GPS data) associated with the user in order to more accurately identify activity segments and/or determine parameters associated with an identified activity segment. In some aspects, location data for the user may be generated, received, or otherwise acquired via the user device 106. For example, in cases where the user device 106 is enabled with GPS capabilities, location data for the user may be determined based on data generated/received via the user device 106. Additionally, or alternatively, the ring 104 may be enabled with GPS or other positioning capabilities. Moreover, in some implementations, location data for a user may be acquired from other wearable devices corresponding to the user, such as a wearable watch device.

Location data may be used to determine one or more parameters associated with an identified activity segment or physical activity. For example, in cases where the system 200 detects that the user went for a run (e.g., running activity segment), location data for the user may be used to determine start/end points for the run, a duration of the run, a route map for the run, and the like. Moreover, location data may be used to determine an elevation change for the run, a pace, an elevation-adjusted pace, and the like. In this regard, leveraging location data along with physiological data collected via the ring 104 may be used to improve activity tracking for the user 102. In some aspects, location data may also be input into the one or more classifiers to further improve activity tracking techniques described herein.

Parameters/characteristics associated with identified activity segments/physical activities which may be determined using acquired physiological data and/or location data may include a type/classification of the physical activity (e.g., walking, running, cycling, swimming), a duration of the activity segment, a distance traveled by the user during the activity segment, an elevation change of the user during the activity segment, a quantity of calories burned by the user during the activity segment, a pace, a speed, a route map, split times/paces, an elevation-adjusted pace, and the like.

For example, the system 200 may identify that the user is engaged in a physical activity (e.g., identify a start of an activity segment) based on acquired physiological data and/or acquired location data, and may determine a first geographical position of the user at the start of the activity segment based on acquired location data for the user. In this example, the system 200 may utilize location information for the user collected throughout the activity segment in order to determine parameters/characteristics of the activity segment, such as pace, distance, speed, a route map, and the like. Similarly, the system 200 may identify a completion of the identified physical activity (e.g., identify a completion of the activity segment) based on acquired physiological data and/or acquired location data, and may determine a second geographical position of the user at the end of the activity segment based on acquired location data for the user. The system 200 may utilize the first and second geographical positions for the user (e.g., starting/ending geographical positions) to further determine parameters/characteristics for the physical activity/activity segment (e.g., route map, distance traveled, etc.).

In some cases, parameters/characteristics for an identified activity segment/physical activity may be dependent on a classification (e.g., type) of the physical activity. For example, if the system 200 detects that the user traveled two miles during a physical activity, the calculated calorie consumption for the physical activity may be drastically different based on whether the user was walking, running, cycling, or swimming. In this regard, the system 200 may receive/generate activity classification data for an identified activity segment, and may determine parameters/characteristics for the identified activity segment based on the activity classification data. Activity classification data may include classified activity types (e.g., walking, running, cycling, swimming), as well as confidence levels (e.g., confidence values/metrics) associated with each respective classified activity type.

For example, the user device 106 may receive physiological data from the ring 104, and may transmit the physiological data to the server 110 for processing. The user device 106 may additionally transmit location data for the user to the server 110. In this example, the server 110 may identify that the user is engaged in physical activity (e.g., identify an activity segment) based on the physiological data and/or location data. The server 110 may additionally generate activity classification data for the activity segment based on the physiological data and/or location data. That is, the server 110 may determine relative confidence levels that the user is engaged in different classified activity types based on the physiological data and/or location data. For instance, the server 110 may determine a 90% confidence level that the user is walking, a 74% confidence level that the user is cycling, and a 10% confidence level that the user is swimming. In this regard, the system 200 may determine parameters for the activity segment based on the activity classification data. In some cases, the server 110 may utilize one or more trained classifiers configured to identify activity segments, activity segment classifications, etc., based on the received physiological data and location data. In some cases, the system 200 may determine parameters/characteristics for the activity segment (e.g., calories burned, intensity) based on a classified activity type with the highest confidence level (e.g., based on the most likely activity type).

The system 200 may leverage both physiological data and location data to determine the activity classification data. For example, the system 200 may identify that a user is engaged in physical activity based on acquired physiological data. In this example, if the system 200 identifies that the user is traveling at a pace of 18 mph using location data for the user, the system 200 may determine that it is more likely that the user is cycling as compared to walking or running, and may therefore generate activity classification data (e.g., classified activity types and corresponding confidence levels) based on the location data and determined pace. In this regard, the location-based activity tracking techniques described herein may enable more efficient and accurate activity classification as compared to some conventional activity tracking techniques.

By way of another example, the system 200 may identify that the user is engaged in physical activity based on acquired physiological data (e.g., increased heart rate, increased temperature, increased respiration rate), but may identify that the user's location is remaining the same (or substantially the same). In this example, the system 200 may identify that the user is running or cycling indoors, such as on a treadmill or stationary bike, as opposed to running/cycling outdoors. Determinations as to whether physical activities are occurring indoors or outdoors may be leveraged to provide more accurate and insightful data, such as more accurate determinations of calorie consumption, more accurate activity classification, etc. By way of another example, the system 200 may identify that the user is engaged in physical activity and that the user's location is continuously changing in a fifty meter-long down-and-back pattern. In this example, the system 200 may utilize the location data to determine that the user is likely swimming. Similarly, if the system 200 identifies that the user is engaged in physical activity and that the user's elevation is substantially changing, the system 200 may identify that the user is skiing or snowboarding. In this regard, the location-based activity tracking techniques described herein may enable more efficient and accurate activity classification as compared to some conventional activity tracking techniques.

In some implementations, upon identifying an activity segment for the user based on acquired physiological data and/or location data for the user, the system 200 may display an indication of the activity segment to the user. For example, the server 110 may cause the user device 106 to display an indication of the identified activity segment via the GUI 275. This may be further shown and described with reference to FIG. 3.

FIG. 3 illustrates an example of a GUI 300 that supports techniques for location-based activity tracking in accordance with aspects of the present disclosure. The GUI 300 may implement, or be implemented by, aspects of the system 100, the system 200, or both. For example, GUI 300 may include an example of the GUI 275 of the user device 106 illustrated in FIG. 2.

The GUI 300 shown in FIG. 3 illustrates a series of application pages 305 which may be displayed to the user via the GUI 300 (e.g., GUI 275 illustrated in FIG. 2). In particular, upon identifying an activity segment for a user, the application page 305-*a* may be presented to the user via the GUI 275 of the user device 106 the next time the user opens the wearable application 250.

As shown in FIG. 3, the application page 305-*a* may include a menu 310, an activity segment card 315, an activity goal progress card 320, and an activities list 325. The menu 310 displayed via the application page 305-*a* may enable users to navigate to view various application pages of the wearable application 250 (e.g., home page, readiness scores, sleep scores, activity scores). The activity goal progress card 320 may display a user's total expended calories for a respective day (e.g., for the current sleep day) relative to the user's calorie consumption goal for the day. The activity goal progress card 320 may also display the user's calculated activity score for the current sleep day, as well as an "inactive time" for the user, which indicates a duration of time during which the user has been inactive for the current sleep day.

Moreover, the GUI 300 may display an indication of an activity segment for the user which is identified by system 200. For example, the application page 305-*a* may display an indication of an activity segment card 315 for the identified activity segment (e.g., walking activity segment).

As shown in FIG. 3, the activity segment card may include a time that the activity segment started (7:09 pm), a time that the activity segment ended, a duration of the identified activity segment (52 minutes), and an estimated calorie consumption during the identified activity segment. In some cases, the activity segment card 315 may display an activity classification/type (e.g., walking) which is associated with a highest confidence level, as described previously herein, in other words, data displayed within the activity segment card 315 (e.g., classified activity type, calories burned, intensity) may be based on a most likely classified activity type for the identified activity segment. Parameters/characteristics of the identified activity segment which are displayed via the activity segment card 315 may be determined based on physiological data acquired from the user during the activity segment, location data for the user during the activity segment, or both.

In some implementations, a user may be able to confirm, dismiss, and/or edit the identified activity segment via the activity segment card 315. For example, as shown in the application page 305-a, the user may be able to select a "confirm" user interface element, in which case the identified activity segment (e.g., walking activity segment) may be added to an activities list 325 in application page 305-a. In this regard, the user may be able to input a confirmation of the activity segment. Upon confirmation of the identified activity segment, the activity segment may be added to the activities list 325, where the user may view and/or edit additional parameters/characteristics of the activity segment.

In some aspects, the system 200 may receive inputs received from the user to further train and improve classifiers used for activity tracking. For example, upon receiving a confirmation of the activity segment (e.g., via the user selecting "confirm"), the system 200 may input the received confirmation into the classifier (e.g., supervised learning) to further train the classifier. Similarly, in cases where the user edits characteristics of the activity segment (e.g., edits a duration of the activity segment, edits a route, edits the activity segment classification), the received user edits may be input into the classifier to further train the classifier to improve future identification of future activity segments.

In some cases, data associated with activity segments included within the activities list 325 may be used to adjust scores for the user (e.g., activity score, readiness score), adjust data displayed within the activity goal progress card 320 (e.g., active calories burned, activity score), and the like. For example, upon confirming the walking activity segment displayed via activity segment card 315, data associated with the walking activity segment (e.g., calories burned, walking duration) may be used to update the user's activity score, readiness score, inactive time, and other scores/parameters for the user for the respective sleep day.

In other cases, the user may be able to select an "edit" user interface element, which may enable the user to edit one or more characteristics of the identified activity segment, such as start/stop times, duration, intensity (e.g., easy, moderate, hard), a classification (e.g., classified activity type) of the identified activity segment, and the like. In other words, the user may be able to selectively modify parameters/characteristics of identified activity segments (e.g., detected physical activity).

For example, upon selection of the "edit" button in the activity segment card 315 or selection of an activity segment within the activity list 315, the GUI 300 may display one or more potential classified activity types for the selected activity segment, and the user may be able to select the correct classified activity type. In cases where the classified activity type selected by the user is different from the displayed activity type (e.g., different from the classified activity type with the highest confidence level), the system 200 may re-calculate parameters/characteristics for the activity segment based on the selected activity type, and display the re-calculated parameters via the GUI 300.

In additional or alternative cases, the system 200 may automatically identify that the user is engaged in physical activity without input from the user. For example, the system 200 may identify an activity segment for the user based on physiological data and/or location data, and without receiving any user input from the user. In such cases, the identified activity segment may be added directly to the confirmed activities list 325, as shown in the application page 305-a. In other words, the system 200 may be configured to identify and track activity segments for the user without receiving manual user inputs from the user.

In cases where the user manually confirms an activity segment (e.g., by selecting "confirm" in the activity segment card 315), the system 200 may be configured to determine parameters/characteristics for an identified activity segment based on a time that the activity segment was first identified, rather than the time that the user confirmed the activity segment. That is, the system 200 may calculate distances, times, calorie consumptions, and other parameters for an identified activity segment from the time that the activity segment began rather than the time the user confirmed the activity segment. Moreover, as noted previously herein, confirmations of detected activity segments may be used to further train classifiers (e.g., machine learning classifiers) which are configured to identify activity segments, and determine characteristics of activity segments.

For example, the system 200 may identify that the user is walking, and may display the activity segment card 315 on application page 305-a. In this example, the user may open the wearable application 250 of the user device 106 ten minutes into the walk to confirm the walk (e.g., via the activity segment card 315), and may walk for an additional twenty minutes (e.g., thirty minute walking activity segment). In this example, the system 200 may be configured to determine a duration of the walk (e.g., 30 minutes), a calorie consumption of the walk, and other parameters for the walk, based on the time that the system 200 first identified the walk, as compared to the time that the user confirmed the walk. That is, the system 200 may calculate parameters for a thirty minute walk based on the time that the user began the walk, rather than a twenty minute walk from the time that the user confirmed the walk. In other words, the system 200 may calculate parameters for the activity segment using physiological data and location data which was collected between a start of the activity segment and a time at which the confirmation was received.

Comparatively, some other activity tracking devices only calculate parameters/characteristics for identified activity segments from the time the user confirms the respective activity segment. Such techniques may lead to inaccurate activity tracking, as these techniques may omit or otherwise disregard physical activity which occurred prior to confirmation of the activity segment. As such, the activity tracking techniques described herein may lead to more accurate and efficient activity tracking.

In some implementations, the system 200 may also automatically detect a completion of an identified activity segment without input from the user. For example, in some cases, the system 200 may identify that the user's temperature and heart rate are both lowering, and may therefore automatically identify a completion of the activity segment. In other words, the system 200 may utilize physiological data collected from the ring 104 to automatically determine that the user is no longer engaged in a physical activity. By way of another example, the system 200 may identify that the user is running (e.g., running activity segment), and may subsequently determine that the user's position has remain unchanged for a threshold period of time (e.g., user is not moving), or that a rate of change of the user's position is less than some threshold (e.g., user is moving at a slow pace). In this example, the system 200 may determine that the user is no longer running based on the location data, and may therefore automatically identify a completion of the activity segment. Accordingly, the system 200 may utilize physiological data, location data, or both, to automatically identify a completion of an identified activity segment.

Comparatively, some conventional wearable devices may require a user to manually indicate an end to a workout. For example, upon completing a run with some conventional wearable devices, a user may have to manually select "end run" in order to finish and confirm the workout. However, users commonly forget to manually indicate a completion to their workouts. In such cases, some conventional wearable devices may continually track the user's movement, etc., and erroneously attribute collected data as being part of the "workout," even long after the user has actually completed the workout. Such erroneous activity tracking may continue until the user notices that their "workout" is still being tracked. This may result in inaccurate activity tracking, as the devices may grossly overestimate the durations of workouts or calories burned during the workouts, or underestimate average pace, etc. As such, by automatically identifying a completion of a workout (e.g., completion of an activity segment) based on collected physiological data and/or location data, aspects of the present disclosure may provide for more efficient and accurate activity monitoring.

In some aspects, a user may be able to select an activity segment within the activity segment card 315 and/or the activities list 325 to view additional information associated with the selected activity segment. For example, upon selection of the running activity segment displayed in the activities list 325 of the application page 305-*a*, the GUI 300 (e.g., GUI 275 of the user device 106 in FIG. 2) may display the application page 305-*b* which illustrates "workout details" for the selected activity segment.

The application page 305-*b* may display one or more parameters or characteristics associated with the running activity segment. For example, the application page 305-*b* may include an activity segment summary card 330 which displays the classified activity type (e.g., running), and a timing of the activity segment (e.g., start time, end time). The application page 305-*b* may further include activity parameter cards 335 which display various parameters/characteristics of the activity segment. For instance, the activity parameter card 335-*a* shows a duration of the activity segment, the activity parameter card 335-*b* shows a quantity of calories burned during the activity segment (e.g., active calories burned), the activity parameter card 335-*c* shows a distance the user ran during the running activity segment, and the activity parameter card 335-*c* shows an average pace throughout the activity segment.

The application page 305-*b* may additionally include a route map card 340 which illustrates the user's route throughout the activity segment. The route map may illustrate the user's starting and ending geographical positions, as well as the user's overall route, which may be determined based on the location data for the user. In some cases, the route map may be overlaid with, or otherwise combined with, a geographical map for the location of the activity segment. For example, the route map may be overlaid on top of a geographical map which is generated or retrieved from Google Maps or another map application.

In some aspects, location information (e.g., route map card 340) may be input into the activity tracking classifiers described herein to improve an identification of future activity segments. In particular, training classifiers using location information, location information may be leveraged by the classifiers to improve activity segment identification, and lead to more accurate determinations of activity segment characteristics (e.g., more accurate determination of calories burned, types of activity segments, routes of workouts, etc.). For example, a user may go on a run every day, and may generally run along three different routes. In this example, the system 200 may train a machine learning classifier to identify the user's workouts (e.g., identify when the user is running) based on acquired physiological data and location data. Further, confirmations and edits received by the user (e.g., the user selecting "confirm" for a detected run) may be used to further train and refine the classifier to improve activity tracking. In this example, the classifier may be configured to associate the user's locations and routes with running activity segments. That is, the machine learning classifier may "learn" that the user is typically running when the user's location moves along one of those three routes. Further, by identifying that the learned routes are generally associated with running workouts for the user, the classifier may be able to predict running workouts along these routes with a higher accuracy and/or confidence score.

Similarly, for a user who typically does indoor cycling workouts, the system 200 may be configured to train a classifier to identify workouts for the user. The classifier may be trained using acquired physiological data, location data, and inputs received from the user (e.g., workout confirmations, edits to workouts). In this example, the classifier may "learn" that the user is likely engaged in a cycling workout if the user's location remains constant (e.g., remains constant at the user's home) and the user's physiological data indicates that the user is engaged in physiological activity. In this regard, the classifier may be able to more accurately identify activity segments for the user, may be able to better differentiate activity segments from non-activity segments, and may be able to more accurately classify and identify parameters for identified activity segments.

The application page 305-*b* may additionally include an activity intensity card 345, which may illustrate a relative intensity of the physical activity throughout the identified activity segment. The activity intensity card 345 may also indicate a relative intensity for the activity segment. For example, the activity intensity card 345 illustrated in the application page 305-*b* indicates a "moderate" intensity for the running activity segment, which may be determined based on the acquired physiological data, location data, or both.

The various parameters/characteristics which are determined for each respective activity segment and displayed to the user via the application pages 305 may vary based on the respective classified activity type. For example, for running activity segments, the application page 305-*b* may display the duration, active calories burned, distance, and average pace of the running activity segment via the activity parameter cards 335, as well as the route map card 340. Comparatively, for hiking activity segments, the application page 305-*b* may display an elevation gain for the activity segment instead of the average pace or some other parameter. For instance, the GUI 300 may display an elevation map for hiking activity segments which illustrates a user's elevation over time throughout the activity segment.

Moreover, in some implementations, the user may be able to customize the "workout details" illustrated in application page 305-*b* for different types of classified activity types. In particular, the user may be able to select which parameters/characteristics are to be displayed for each respective classified activity type. For example, the user may select a first set of parameters which are to be displayed for running activity segments (e.g., duration, calories burned, distance, average pace, top speed, split times/paces, elevation-adjusted pace), and a second set of parameters which are to be displayed for hiking activity segments (e.g., duration, distance, elevation gain).

The collection and utilization of location data within the system 200 may enable improved activity tracking, and may enable other unique features and use cases. As location data for a given user is collected and analyzed over time (for example, in the context of location-based activity tracking), the system 200 may be able to improve a quality of activity segment predictions and activity segment analysis by supplementing accelerometer data with more context (e.g., is the user cycling on a local road, or driving on packed highway?), and by adding semantic understanding of user location (e.g., is the user at home or the gym?). Moreover, as the system 200 collects location data for the user, the system 200 may be able to more efficiently differentiate between indoor and outdoor workouts, such as indoor spin classes and cycling to the office.

Moreover, the collection and analysis of a user's location data may enable a wide range of additional functionality and use cases which may be used to improve other functions performed by the system 200, such as sleep tracking. Additional functionality which may be enabled by collecting location data for a user may include jet lag prediction and preparation, daylight savings prediction and preparation, altitude/elevation sickness prediction and preparation, determinations of sunlight/sunset (which may be used to adjust bedtime and wake time recommendations), air quality alerts, weather alerts and impacts, and the like.

Moreover, in some aspects, the collection and analysis of a user's location data may enable helpful and more insightful insights and guidance regarding a user's activity scores, readiness scores, exertion, and overall health. In particular, by leveraging location data, the system 200 may be able to more accurately determine whether physiological data and scores (e.g., sleep score, readiness score, activity score) for a given user are attributable to the user's overall activity and sleep, or whether characteristics associated with location (e.g., elevation, time changes, jet lag) have played a role in the user's physiological data and respective scores.

For example, a user may travel from their home in a low to mid elevation up to the mountains (e.g., high elevation), and may exercise in the mountains. In this example, the user's physiological data (e.g., HRV, heart rate, respiration rate) may suggest, or otherwise lead to, poor sleep and readiness scores due to the higher elevation and lower oxygen content at higher elevations. Even if the user may have slept or otherwise have recovered well, the abnormal physiological data may indicate that their body is struggling due to external factors (e.g., higher elevation) rather than internal factors. Accordingly, by analyzing the user's location in conjunction with other data (e.g., physiological data collected from the user), the system 200 may be able to determine that the user's abnormal physiological data (and therefore decreased sleep/readiness scores) is likely attributable to the user traveling from a low/mid elevation to a higher elevation, and not due to, for example, over-training, insufficient recovery, or other internal factors. Moreover, at higher elevations, a user may have to work harder as compared to lower elevations (e.g., it is harder to run a mile at higher elevations as compared to lower elevations). In such cases, the system 200 may be able to selectively adjust the sleep/readiness scores based on the user's location data (e.g., selectively increase a user's activity score based on the user performing an activity at a higher elevation).

Additionally, or alternatively, the system 200 may be configured to provide more insightful messaging to the user regarding a potential impact of the higher elevation on the user's physiological data and/or scores. For instance, the system 200 may display a message which states "Your sleep and readiness scores are lower than usual. This may be due to traveling to a higher elevation." Location analysis techniques described herein may also provide more insightful messaging related to activity and exertion, such as messages which acknowledge that activity performed at higher elevations may result in higher calorie consumptions, higher activity scores, and the like.

In some implementations, the system 200 may request permission to access location data for users, and may only begin tracking location data for a user when the respective user has confirmed or approved location tracking. This may be further shown and described with reference to FIG. 4.

Figure 4:
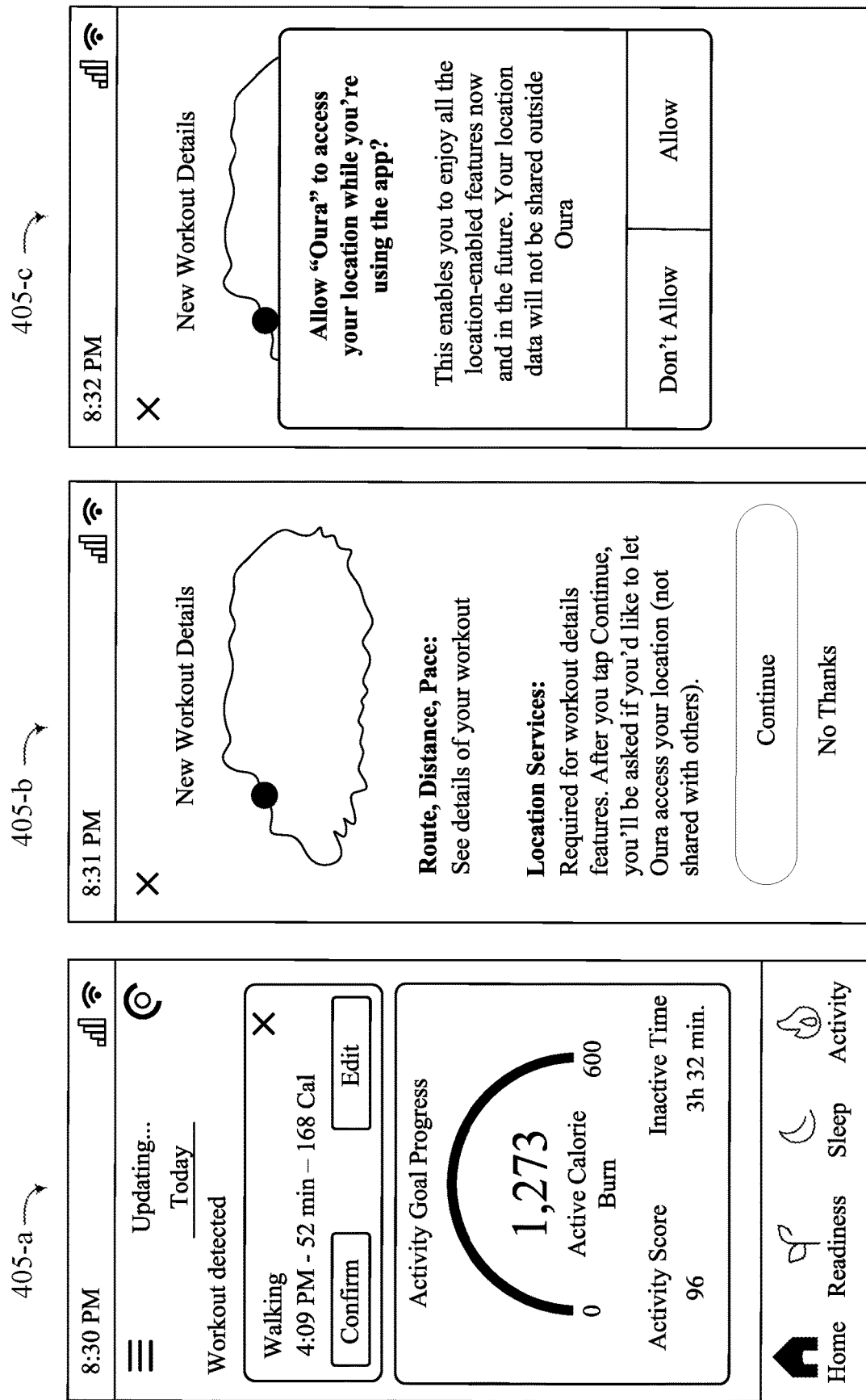
FIG. 4 illustrates an example of a GUI that supports techniques for location-based activity tracking in accordance with aspects of the present disclosure.

FIG. 4 illustrates an example of a GUI 400 that supports techniques for location-based activity tracking in accordance with aspects of the present disclosure. The GUI 300 may implement, or be implemented by, aspects of the system 100, the system 200, or both. For example, GUI 400 may include an example of the GUI 275 of the user device 106 illustrated in FIG. 2.

The GUI 400 in FIG. 4 illustrates a series of application pages 405 which may be displayed to the user via the GUI 400 (e.g., GUI 275 illustrated in FIG. 2). In particular, the application pages 405 illustrated in FIG. 4 may illustrate application pages which are displayed to the user via the GUI 275 of the user device 106 when requesting access to track location data for the user.

For example, a user may update the wearable application 250 on their user device 106 to a version of the wearable application 250 which supports location tracking, and may subsequently perform a workout (e.g., activity segment). Upon opening the wearable application 250 after the workout, the user may be presented with the application page 405-*a*, which illustrates that a workout (e.g., activity segment) has been detected. Upon confirming the activity segment/workout displayed on the application page 405-*a*, the GUI 400 may display the application page 405-*b*. Additionally, or alternatively, in cases where activity segments/workouts are automatically detected by the system 200, the application page 405-*b* may be displayed to the user upon opening the wearable application 250 for the first time following the workout.

Application page 405-*b* illustrates an information card which describes how location tracking may be used to supplement and improve activity tracking features which are performed by the system 200. The user may be able to opt-out or confirm/approve the location-tracking features via application page 405-*b* (e.g., select "No thanks" or "Continue").

In cases where the user approves the location-tracking features (e.g., selects "Continue" on application page 405-*b*), the GUI 400 may display application page 405-*c*. Application page 405-c may include a system-level permission prompt associated with the user device 106 in which the user may again select to opt-out or confirm/approve the location-tracking features. As compared to the prompt shown in application page 405-b, which may request permission for the wearable application 250 to track the user's location, the prompt shown in application page 405-c may include a request generated by the operating system of the user device 106. In some implementations, the system 200 may only begin tracking the user's location data if the user confirms/approves the use of location-tracking features via the application page 405-b, application page 405-c, or both.

In some aspects, the use of the application pages 405-a, 405-b, and 405-c may ensure user privacy by enabling users to know exactly how their location data may be used. The application pages 405 may include information which states that the user's location data will not be shared with third parties or other users, along with other information regarding how the location data will be used. For example, the application pages 405 may include additional prompts or requests that the user's location data be used in anonymized studies to improve various functions and features performed by the system 200. In cases where a user declines the system 200 to track their location data, the user may be able to later opt-in to the location-tracking features via the user device 106 (e.g., via wearable application 250). Conversely, users who opted-in to location tracking features may be able to later opt-out via the user device 106.

Figure 5:
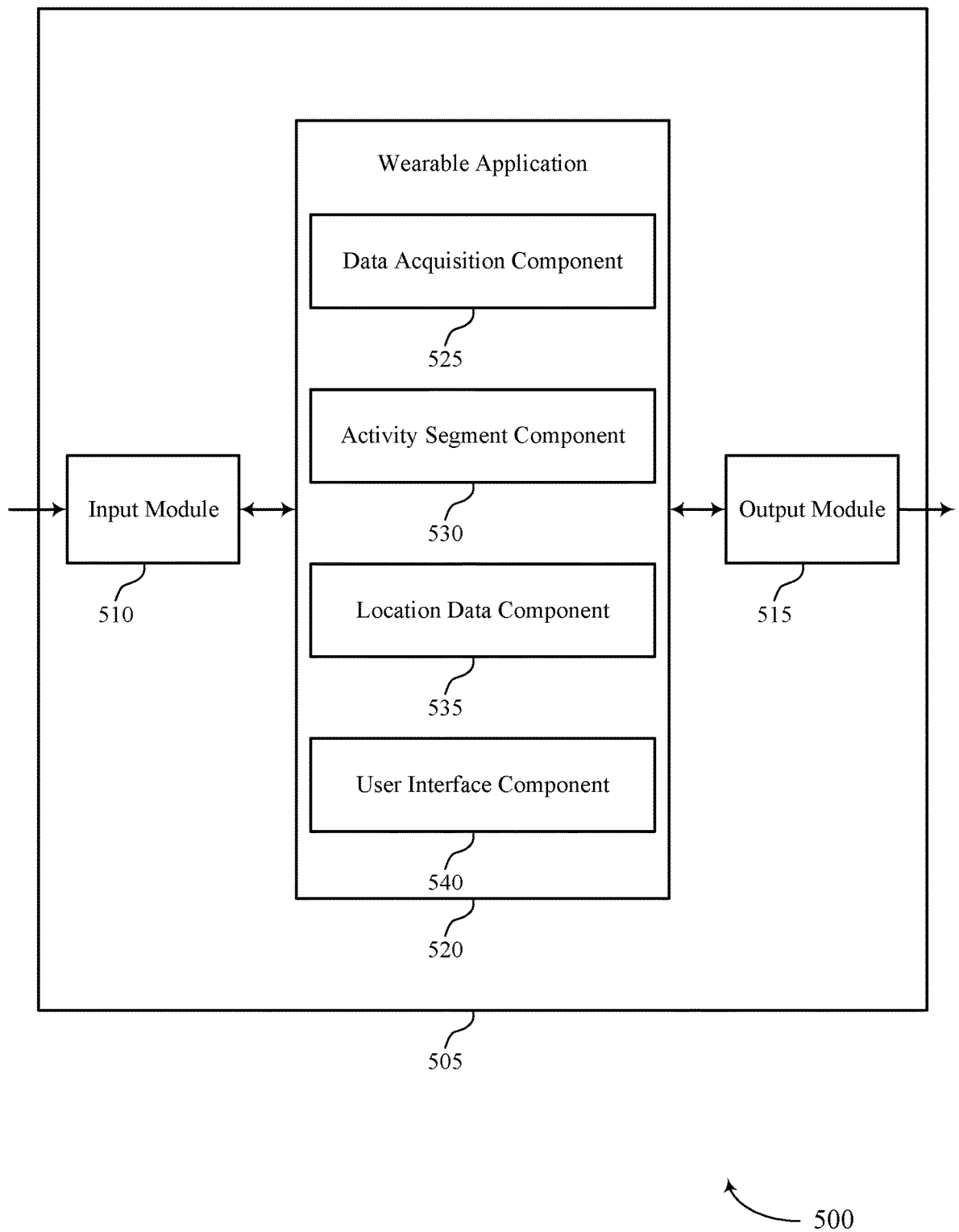
FIG. 5 shows a block diagram of an apparatus that supports techniques for location-based activity tracking in accordance with aspects of the present disclosure.

FIG. 5 shows a block diagram 500 of a device 505 that supports techniques for location-based activity tracking in accordance with aspects of the present disclosure. In some aspects, the device 505 may include an example of a user device 106, as shown and described with reference to FIGS. 1-4. The device 505 may include an input module 510, an output module 515, and a wearable application 520. The device 505 may also include a processor. Each of these components may be in communication with one another (e.g., via one or more buses).

The input module 510 may provide a means for receiving information such as packets, user data, control information, or any combination thereof associated with various information channels (e.g., control channels, data channels, information channels related to illness detection techniques). Information may be passed on to other components of the device 505. The input module 510 may utilize a single antenna or a set of multiple antennas.

The output module 515 may provide a means for transmitting signals generated by other components of the device 505. For example, the output module 515 may transmit information such as packets, user data, control information, or any combination thereof associated with various information channels (e.g., control channels, data channels, information channels related to illness detection techniques). In some examples, the output module 515 may be co-located with the input module 510 in a transceiver module. The output module 515 may utilize a single antenna or a set of multiple antennas.

For example, the wearable application 520 may include a data acquisition component 525, an activity segment component 530, a location data component 535, a user interface component 540, or any combination thereof. In some examples, the wearable application 520, or various components thereof, may be configured to perform various operations (e.g., receiving, monitoring, transmitting) using or otherwise in cooperation with the input module 510, the output module 515, or both. For example, the wearable application 520 may receive information from the input module 510, send information to the output module 515, or be integrated in combination with the input module 510, the output module 515, or both to receive information, transmit information, or perform various other operations as described herein.

The wearable application 520 may support automatic activity detection in accordance with examples as disclosed herein. The data acquisition component 525 may be configured as or otherwise support a means for receiving physiological data associated with a user from a wearable device. The activity segment component 530 may be configured as or otherwise support a means for identifying, based at least in part on the physiological data, an activity segment during which the user is engaged in a physical activity. The location data component 535 may be configured as or otherwise support a means for identifying location data associated with the user for at least a portion of the activity segment. The activity segment component 530 may be configured as or otherwise support a means for identifying one or more parameters associated with the physical activity based at least in part on the physiological data and the location data. The user interface component 540 may be configured as or otherwise support a means for causing a GUI of a user device to display the one or more parameters associated with the physical activity.

Figure 6:
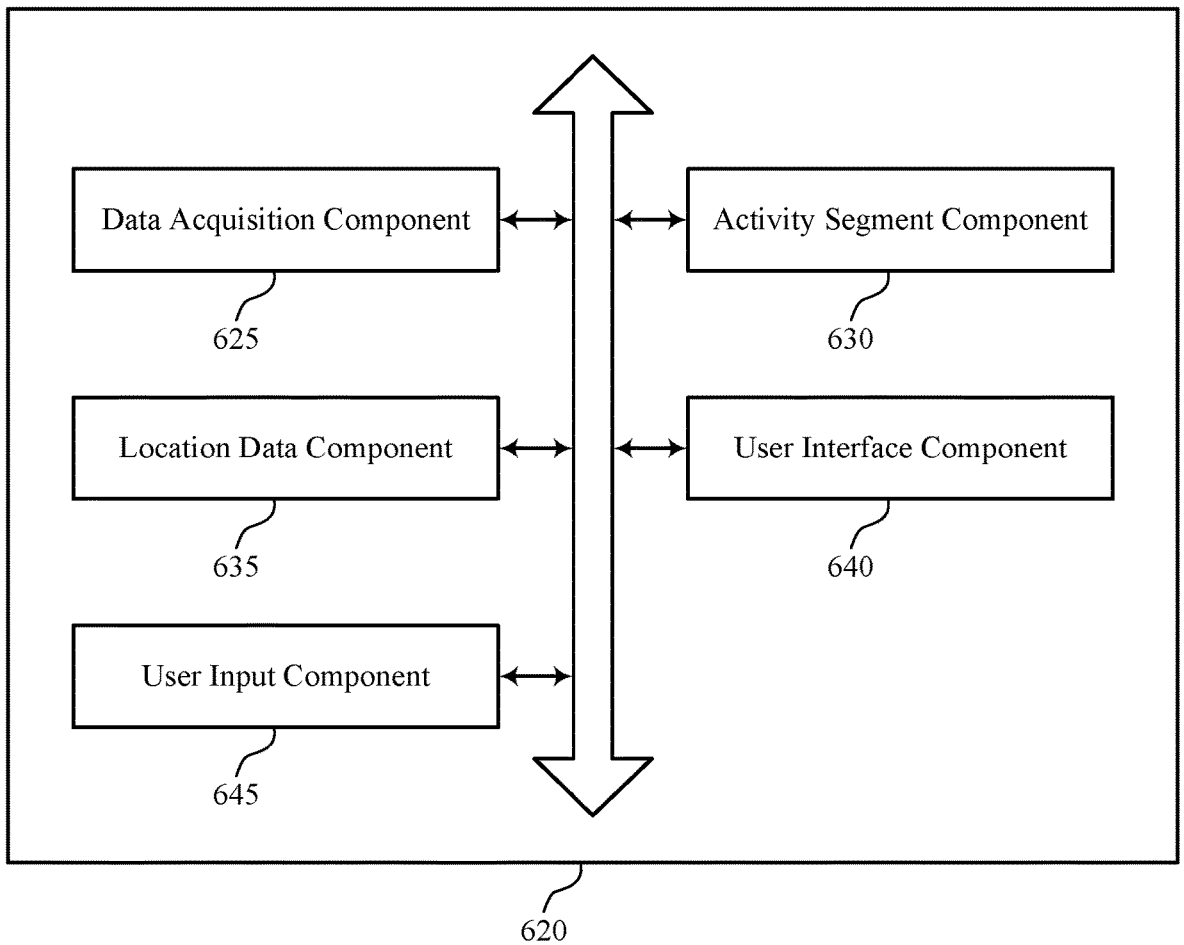
FIG. 6 shows a block diagram of a wearable application that supports techniques for location-based activity tracking in accordance with aspects of the present disclosure.

FIG. 6 shows a block diagram 600 of a wearable application 620 that supports techniques for location-based activity tracking in accordance with aspects of the present disclosure. The wearable application 620 may be an example of aspects of a wearable application or a wearable application 520, or both, as described herein. The wearable application 620, or various components thereof, may be an example of means for performing various aspects of location-based activity tracking as described herein. For example, the wearable application 620 may include a data acquisition component 625, an activity segment component 630, a location data component 635, a user interface component 640, a user input component 645, or any combination thereof. Each of these components may communicate, directly or indirectly, with one another (e.g., via one or more buses).

The wearable application 620 may support automatic activity detection in accordance with examples as disclosed herein. The data acquisition component 625 may be configured as or otherwise support a means for receiving physiological data associated with a user from a wearable device. The activity segment component 630 may be configured as or otherwise support a means for identifying, based at least in part on the physiological data, an activity segment during which the user is engaged in a physical activity. The location data component 635 may be configured as or otherwise support a means for identifying location data associated with the user for at least a portion of the activity segment. In some examples, the activity segment component 630 may be configured as or otherwise support a means for identifying one or more parameters associated with the physical activity based at least in part on the physiological data and the location data. The user interface component 640 may be configured as or otherwise support a means for causing a GUI of a user device to display the one or more parameters associated with the physical activity.

In some examples, the user interface component 640 may be configured as or otherwise support a means for causing the GUI of the user device to display an indication of the activity segment. In some examples, the user input component 645 may be configured as or otherwise support a means for receiving, via the user device and in response to the indication of the activity segment, a confirmation of the activity segment, where causing the GUI to display the one or more parameters associated with the physical activity is based at least in part on receiving the confirmation.

In some examples, to support identifying the one or more parameters associated with the physical activity, the activity segment component 630 may be configured as or otherwise support a means for identifying the one or more parameters associated with the physical activity based at least in part on physiological data and location data associated with a portion of the activity segment between the start of the activity segment and receipt of the confirmation.

In some examples, the activity segment component 630 may be configured as or otherwise support a means for automatically identifying a completion of the activity segment based at least in part on the received physiological data, where causing the GUI to display the one or more parameters associated with the physical activity is based at least in part on automatically identifying the completion of the activity segment.

In some examples, the user input component 645 may be configured as or otherwise support a means for receiving, via the user device, a user input which selectively modifies at least one parameter of the one or more parameters associated with the physical activity.

In some examples, the one or more parameters associated with the physical activity include a type of the physical activity, a duration of the activity segment, a distance traveled by the user during the activity segment, an elevation change of the user during the activity segment, a quantity of calories burned by the user during the activity segment, or any combination thereof. In some examples, the one or more parameters associated with the physical activity include a pace, a speed, an elevation, a route map, a split time, an elevation-adjusted pace, or any combination thereof.

In some examples, the location data component 635 may be configured as or otherwise support a means for identifying a first geographical position of the user at a start of the activity segment and a second geographical position of the user at an end of the activity segment, where identifying the one or more parameters associated with the physical activity is based at least in part on the first geographical position, the second geographical position, or both.

In some examples, the activity segment component 630 may be configured as or otherwise support a means for receiving, from a server, activity classification data associated with the activity segment, the activity classification data including a plurality of classified activity types and corresponding confidence values, the confidence values indicating a confidence level associated with the corresponding classified activity type, where identifying the one or more parameters associated with the physical activity is based at least in part on receiving the activity classification data.

In some examples, the user interface component 640 may be configured as or otherwise support a means for causing the GUI of the user device to display one or more classified activity types of the plurality of classified activity types based at least in part on receiving the activity classification data. In some examples, the user input component 645 may be configured as or otherwise support a means for receiving, via the user device and in response to displaying the one or more classified activity types, a selection of a classified activity type of the one or more classified activity types, where identifying the one or more parameters associated with the physical activity is based at least in part on receiving the selection.

In some examples, the physiological data includes temperature data, accelerometer data, heart rate data, respiratory rate data, or any combination thereof. In some examples, the wearable device includes a wearable ring device. In some examples, the wearable device collects the physiological data from the user using based on arterial blood flow.

Figure 7:
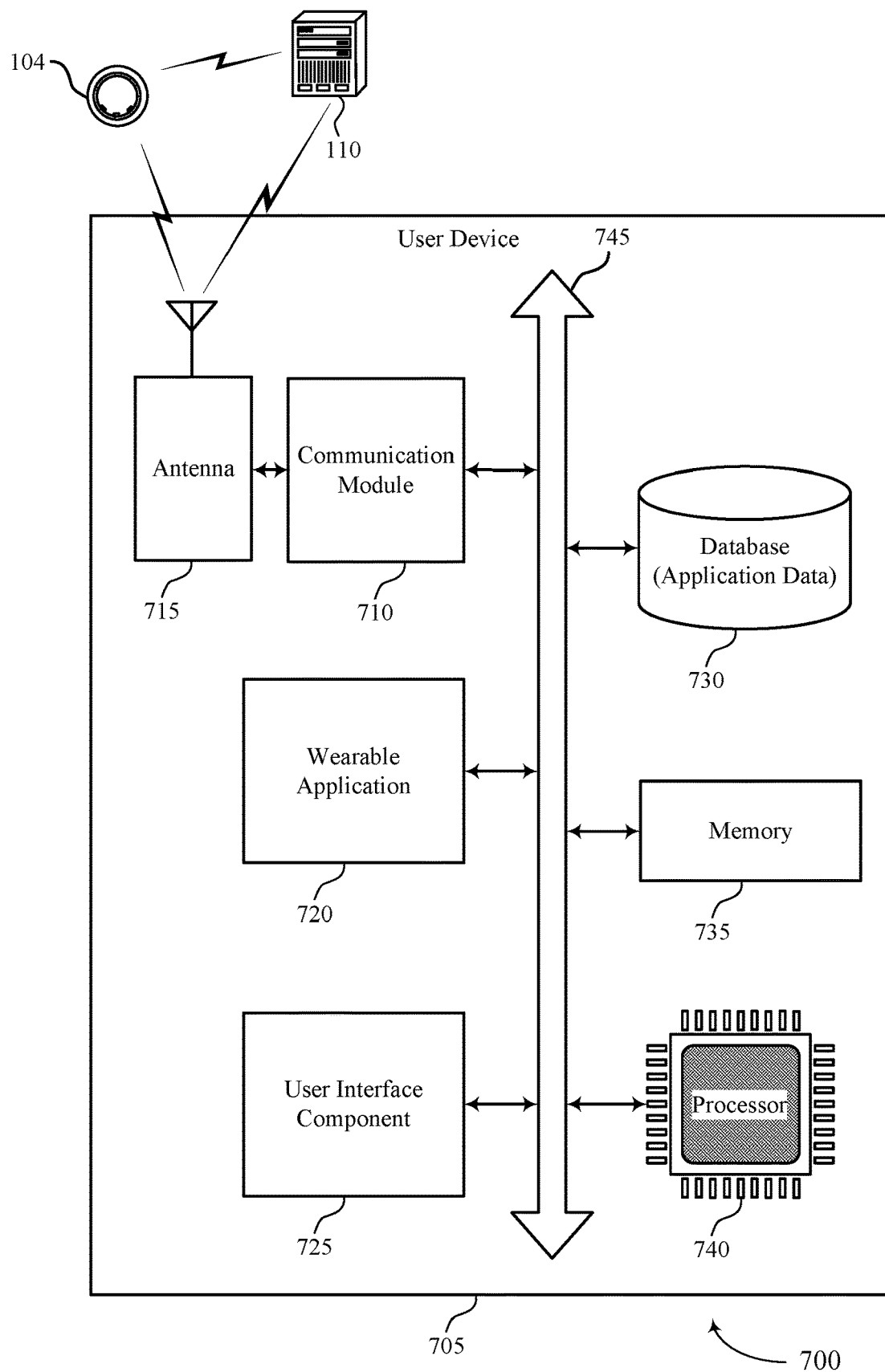
FIG. 7 shows a diagram of a system including a device that supports techniques for location-based activity tracking in accordance with aspects of the present disclosure.

FIG. 7 shows a diagram of a system 700 including a device 705 that supports techniques for location-based activity tracking in accordance with aspects of the present disclosure. The device 705 may be an example of or include the components of a device 505 as described herein. The device 705 may include an example of a user device 106, as described previously herein with reference to FIGS. 1-6. The device 705 may include components for bi-directional communications with a wearable device (e.g., ring 104) and servers 110, including components for transmitting and receiving communications, such as a wearable application 720, a communication module 710, an antenna 715, a user interface component 725, a database (application data) 730, a memory 735, and a processor 740. These components may be in electronic communication or otherwise coupled (e.g., operatively, communicatively, functionally, electronically, electrically) via one or more buses (e.g., a bus 745).

The communication module 710 may manage input and output signals for the device 705 via the antenna 715. The communication module 710 may include an example of the communication module 220-b of the user device 106 shown and described in FIG. 2. In this regard, the communication module 710 may manage communications with the ring 104 and the server 110, as illustrated in FIG. 2. The communication module 710 may also manage peripherals not integrated into the device 705. In some cases, the communication module 710 may represent a physical connection or port to an external peripheral. In some cases, the communication module 710 may utilize an operating system such as iOSR, ANDROIDR, MS-DOS R, MS-WINDOWS®, OS/2R, UNIXR, LINUXR, or another known operating system. In other cases, the communication module 710 may represent or interact with a wearable device (e.g., ring 104), modem, a keyboard, a mouse, a touchscreen, or a similar device. In some cases, the communication module 710 may be implemented as part of the processor 740. In some examples, a user may interact with the device 705 via the communication module 710, user interface component 725, or via hardware components controlled by the communication module 710.

In some cases, the device 705 may include a single antenna 715. However, in some other cases, the device 705 may have more than one antenna 715, which may be capable of concurrently transmitting or receiving multiple wireless transmissions. The communication module 710 may communicate bi-directionally, via the one or more antennas 715, wired, or wireless links as described herein. For example, the communication module 710 may represent a wireless transceiver and may communicate bi-directionally with another wireless transceiver. The communication module 710 may also include a modem to modulate the packets, to provide the modulated packets to one or more antennas 715 for transmission, and to demodulate packets received from the one or more antennas 715.

The user interface component 725 may manage data storage and processing in a database 730. In some cases, a user may interact with the user interface component 725. In other cases, the user interface component 725 may operate automatically without user interaction. The database 730 may be an example of a single database, a distributed database, multiple distributed databases, a data store, a data lake, or an emergency backup database.

The memory 735 may include RAM and ROM. The memory 735 may store computer-readable, computer-executable software including instructions that, when executed, cause the processor 740 to perform various functions described herein. In some cases, the memory 735 may contain, among other things, a basic I/O system (BIOS) which may control basic hardware or software operation such as the interaction with peripheral components or devices.

The processor 740 may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 740 may be configured to operate a memory array using a memory controller. In other cases, a memory controller may be integrated into the processor 740. The processor 740 may be configured to execute computer-readable instructions stored in a memory 735 to perform various functions (e.g., functions or tasks supporting a method and system for sleep staging algorithms).

The wearable application 720 may support automatic activity detection in accordance with examples as disclosed herein. For example, the wearable application 720 may be configured as or otherwise support a means for receiving physiological data associated with a user from a wearable device. The wearable application 720 may be configured as or otherwise support a means for identifying, based at least in part on the physiological data, an activity segment during which the user is engaged in a physical activity. The wearable application 720 may be configured as or otherwise support a means for identifying location data associated with the user for at least a portion of the activity segment. The wearable application 720 may be configured as or otherwise support a means for identifying one or more parameters associated with the physical activity based at least in part on the physiological data and the location data. The wearable application 720 may be configured as or otherwise support a means for causing a GUI of a user device to display the one or more parameters associated with the physical activity.

By including or configuring the wearable application 720 in accordance with examples as described herein, the device 705 may support techniques for improved activity detection. In particular, techniques descried herein may facilitate improved activity data tracking by leveraging location data associated with detected activities. By leveraging location data to improve activity tracking, techniques described herein may provide users with more accurate and useful information regarding their activities, which may facilitate increased user activity and engagement, and facilitate more efficient activity training programs.

The wearable application 720 may include an application (e.g., "app"), program, software, or other component which is configured to facilitate communications with a ring 104, server 110, other user devices 106, and the like. For example, the wearable application 720 may include an application executable on a user device 106 which is configured to receive data (e.g., physiological data) from a ring 104, perform processing operations on the received data, transmit and receive data with the servers 110, and cause presentation of data to a user 102.

Figure 8:
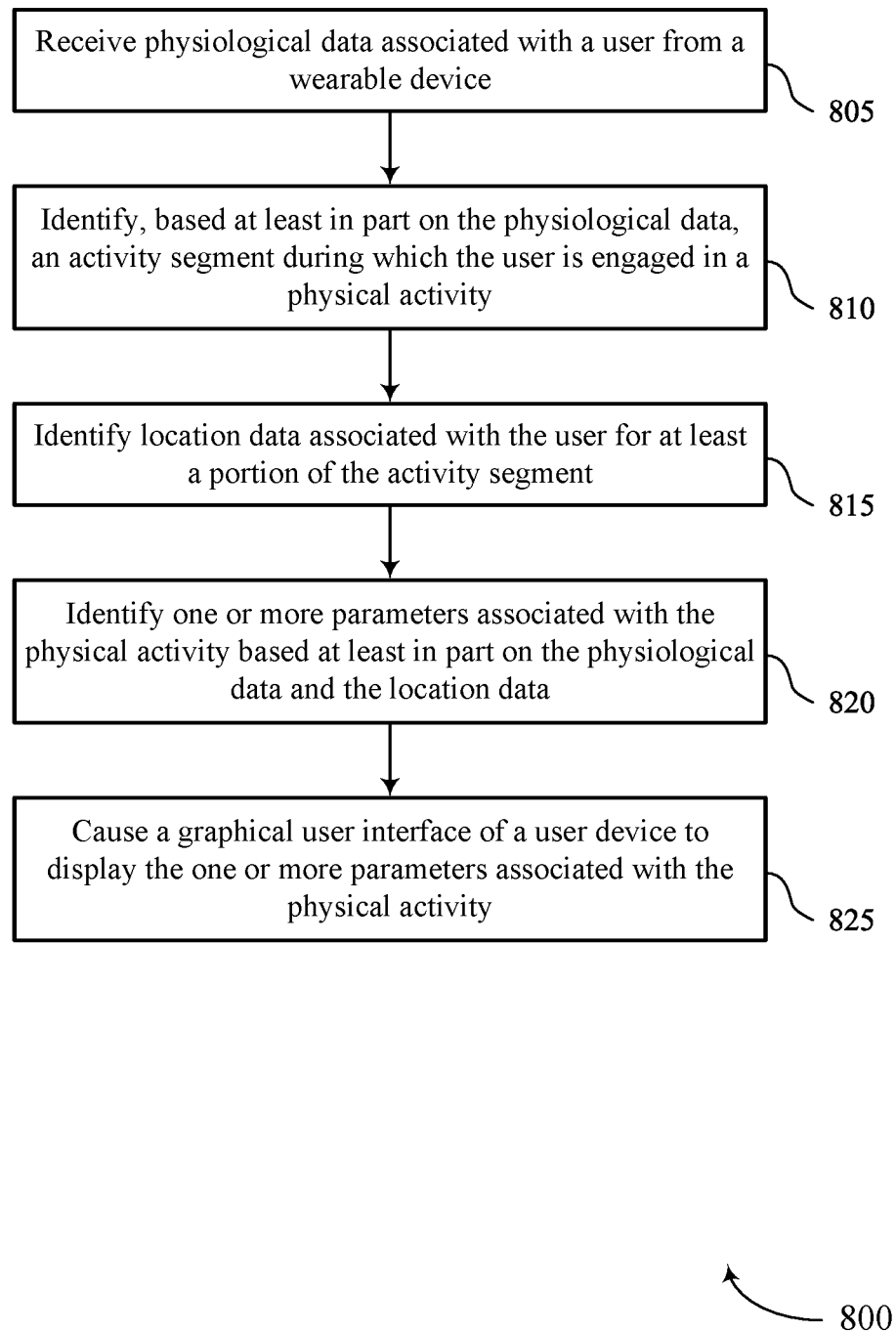
FIGS. 8 through 10 show flowcharts illustrating methods that support location-based activity tracking in accordance with aspects of the present disclosure.

FIG. 8 shows a flowchart illustrating a method 800 that supports techniques for location-based activity tracking in accordance with aspects of the present disclosure.

The operations of the method 800 may be implemented by a user device or its components as described herein. For example, the operations of the method 800 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 805, the method may include receiving physiological data associated with a user from a wearable device. The operations of 805 may be performed in accordance with examples as disclosed herein. In some examples, aspects of the operations of 805 may be performed by a data acquisition component 625 as described with reference to FIG. 6.

At 810, the method may include identifying, based at least in part on the physiological data, an activity segment during which the user is engaged in a physical activity. The operations of 810 may be performed in accordance with examples as disclosed herein. In some examples, aspects of the operations of 810 may be performed by an activity segment component 630 as described with reference to FIG. 6.

At 815, the method may include identifying location data associated with the user for at least a portion of the activity segment. The operations of 815 may be performed in accordance with examples as disclosed herein. In some examples, aspects of the operations of 815 may be performed by a location data component 635 as described with reference to FIG. 6.

At 820, the method may include identifying one or more parameters associated with the physical activity based at least in part on the physiological data and the location data. The operations of 820 may be performed in accordance with examples as disclosed herein. In some examples, aspects of the operations of 820 may be performed by an activity segment component 630 as described with reference to FIG. 6.

At 825, the method may include causing a GUI of a user device to display the one or more parameters associated with the physical activity. The operations of 825 may be performed in accordance with examples as disclosed herein. In some examples, aspects of the operations of 825 may be performed by a user interface component 640 as described with reference to FIG. 6.

Figure 9:
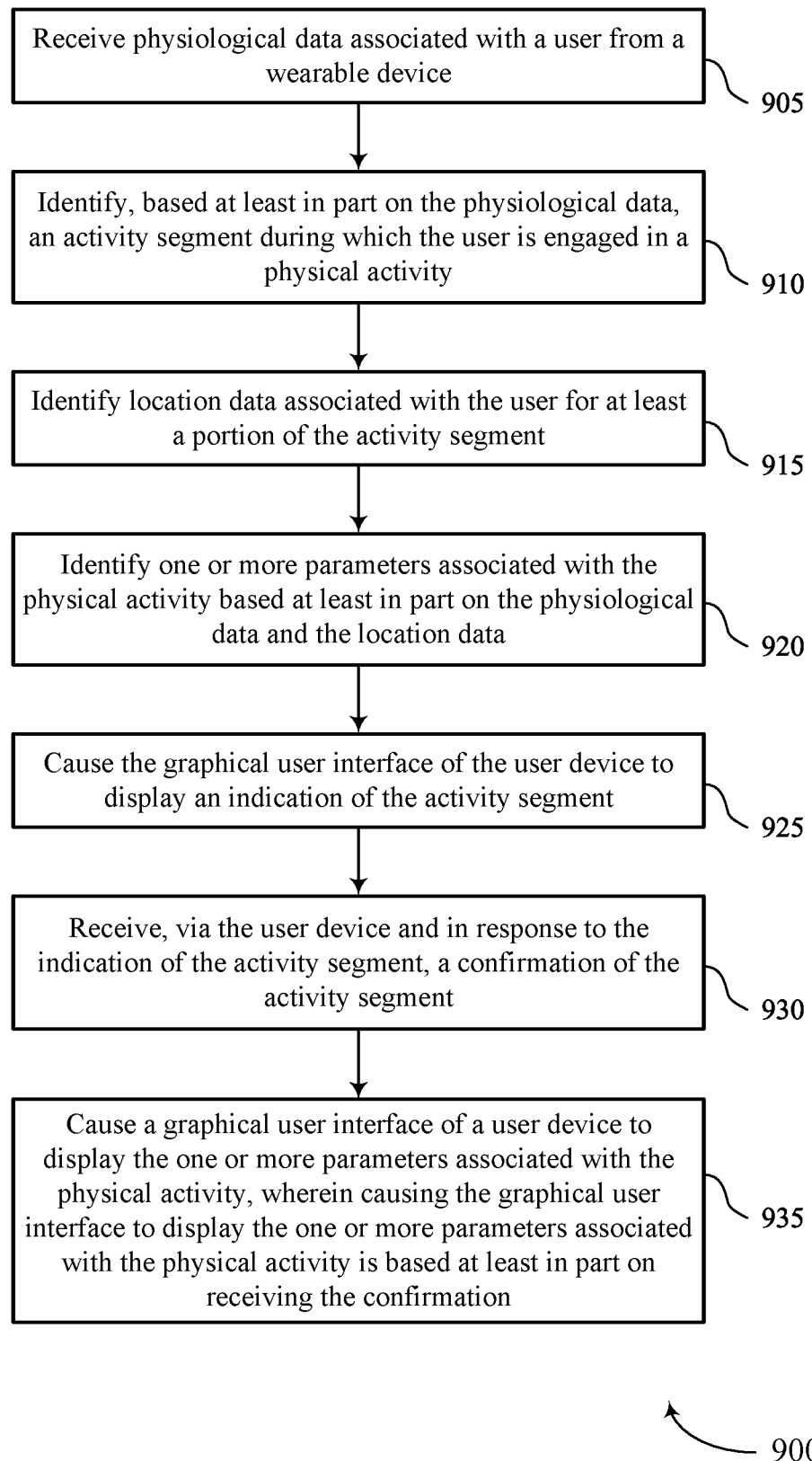

FIG. 9 shows a flowchart illustrating a method 900 that supports techniques for location-based activity tracking in accordance with aspects of the present disclosure. The operations of the method 900 may be implemented by a user device or its components as described herein. For example, the operations of the method 900 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 905, the method may include receiving physiological data associated with a user from a wearable device. The operations of 905 may be performed in accordance with examples as disclosed herein. In some examples, aspects of the operations of 905 may be performed by a data acquisition component 625 as described with reference to FIG. 6.

At 910, the method may include identifying, based at least in part on the physiological data, an activity segment during which the user is engaged in a physical activity. The operations of 910 may be performed in accordance with examples as disclosed herein. In some examples, aspects of the operations of 910 may be performed by an activity segment component 630 as described with reference to FIG. 6.

At 915, the method may include identifying location data associated with the user for at least a portion of the activity segment. The operations of 915 may be performed in accordance with examples as disclosed herein. In some examples, aspects of the operations of 915 may be performed by a location data component 635 as described with reference to FIG. 6.

At 920, the method may include identifying one or more parameters associated with the physical activity based at least in part on the physiological data and the location data. The operations of 920 may be performed in accordance with examples as disclosed herein. In some examples, aspects of the operations of 920 may be performed by an activity segment component 630 as described with reference to FIG. 6. At 925, the method may include causing the GUI of the user device to display an indication of the activity segment. The operations of 925 may be performed in accordance with examples as disclosed herein. In some examples, aspects of the operations of 925 may be performed by a user interface component 640 as described with reference to FIG. 6.

At 930, the method may include receiving, via the user device and in response to the indication of the activity segment, a confirmation of the activity segment. The operations of 930 may be performed in accordance with examples as disclosed herein. In some examples, aspects of the operations of 930 may be performed by a user input component 645 as described with reference to FIG. 6.

At 935, the method may include causing a GUI of a user device to display the one or more parameters associated with the physical activity, where causing the GUI to display the one or more parameters associated with the physical activity is based at least in part on receiving the confirmation. The operations of 935 may be performed in accordance with examples as disclosed herein. In some examples, aspects of the operations of 935 may be performed by a user interface component 640 as described with reference to FIG. 6.

Figure 10:
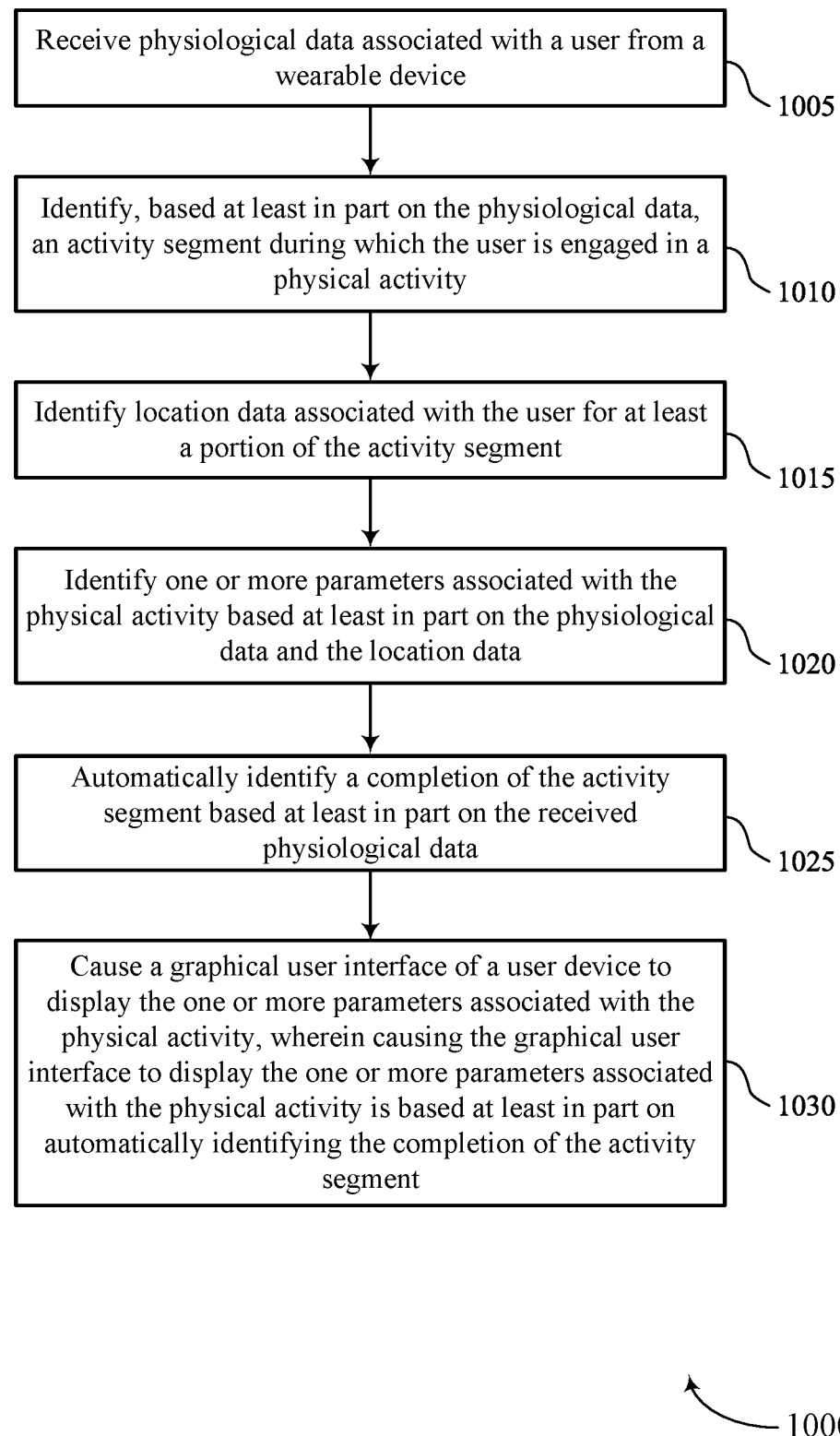

FIG. 10 shows a flowchart illustrating a method 1000 that supports techniques for location-based activity tracking in accordance with aspects of the present disclosure. The operations of the method 1000 may be implemented by a user device or its components as described herein. For example, the operations of the method 1000 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 1005, the method may include receiving physiological data associated with a user from a wearable device. The operations of 1005 may be performed in accordance with examples as disclosed herein. In some examples, aspects of the operations of 1005 may be performed by a data acquisition component 625 as described with reference to FIG. 6.

At 1010, the method may include identifying, based at least in part on the physiological data, an activity segment during which the user is engaged in a physical activity. The operations of 1010 may be performed in accordance with examples as disclosed herein. In some examples, aspects of the operations of 1010 may be performed by an activity segment component 630 as described with reference to FIG. 6.

At 1015, the method may include identifying location data associated with the user for at least a portion of the activity segment. The operations of 1015 may be performed in accordance with examples as disclosed herein. In some examples, aspects of the operations of 1015 may be performed by a location data component 635 as described with reference to FIG. 6.

At 1020, the method may include identifying one or more parameters associated with the physical activity based at least in part on the physiological data and the location data. The operations of 1020 may be performed in accordance with examples as disclosed herein. In some examples, aspects of the operations of 1020 may be performed by an activity segment component 630 as described with reference to FIG. 6.

At 1025, the method may include automatically identifying a completion of the activity segment based at least in part on the received physiological data. The operations of 1025 may be performed in accordance with examples as disclosed herein. In some examples, aspects of the operations of 1025 may be performed by an activity segment component 630 as described with reference to FIG. 6.

At 1030, the method may include causing a GUI of a user device to display the one or more parameters associated with the physical activity, where causing the GUI to display the one or more parameters associated with the physical activity is based at least in part on automatically identifying the completion of the activity segment. The operations of 1030 may be performed in accordance with examples as disclosed herein. In some examples, aspects of the operations of 1030 may be performed by a user interface component 640 as described with reference to FIG. 6.

A method for automatic activity detection is described. The method may include receiving physiological data associated with a user from a wearable device, identifying, based at least in part on the physiological data, an activity segment during which the user is engaged in a physical activity, identifying location data associated with the user for at least a portion of the activity segment, identifying one or more parameters associated with the physical activity based at least in part on the physiological data and the location data, and causing a GUI of a user device to display the one or more parameters associated with the physical activity.

An apparatus for automatic activity detection is described. The apparatus may include a processor, memory coupled with the processor, and instructions stored in the memory. The instructions may be executable by the processor to cause the apparatus to receive physiological data associated with a user from a wearable device, identify, based at least in part on the physiological data, an activity segment during which the user is engaged in a physical activity, identify location data associated with the user for at least a portion of the activity segment, identify one or more parameters associated with the physical activity based at least in part on the physiological data and the location data, and cause a GUI of a user device to display the one or more parameters associated with the physical activity.

Another apparatus for automatic activity detection is described. The apparatus may include means for receiving physiological data associated with a user from a wearable device, means for identifying, based at least in part on the physiological data, an activity segment during which the user is engaged in a physical activity, means for identifying location data associated with the user for at least a portion of the activity segment, means for identifying one or more parameters associated with the physical activity based at least in part on the physiological data and the location data, and means for causing a GUI of a user device to display the one or more parameters associated with the physical activity.

A non-transitory computer-readable medium storing code for automatic activity detection is described. The code may include instructions executable by a processor to receive physiological data associated with a user from a wearable device, identify, based at least in part on the physiological data, an activity segment during which the user is engaged in a physical activity, identify location data associated with the user for at least a portion of the activity segment, identify one or more parameters associated with the physical activity based at least in part on the physiological data and the location data, and cause a GUI of a user device to display the one or more parameters associated with the physical activity.

Some examples of the method, apparatuses, and non-transitory computer-readable medium described herein may further include operations, features, means, or instructions for causing the GUI of the user device to display an indication of the activity segment and receiving, via the user device and in response to the indication of the activity segment, a confirmation of the activity segment, wherein causing the GUI to display the one or more parameters associated with the physical activity may be based at least in part on receiving the confirmation.

In some examples of the method, apparatuses, and non-transitory computer-readable medium described herein, identifying the one or more parameters associated with the physical activity may include operations, features, means, or instructions for identifying the one or more parameters associated with the physical activity based at least in part on physiological data and location data associated with a portion of the activity segment between the start of the activity segment and reception of the confirmation.

In some examples of the method, apparatuses, and non-transitory computer-readable medium described herein, automatically identifying a completion of the activity segment based at least in part on the received physiological data, wherein causing the GUI to display the one or more parameters associated with the physical activity may be based at least in part on automatically identifying the completion of the activity segment.

Some examples of the method, apparatuses, and non-transitory computer-readable medium described herein may further include operations, features, means, or instructions for receiving, via the user device, a user input which selectively modifies at least one parameter of the one or more parameters associated with the physical activity.

In some examples of the method, apparatuses, and non-transitory computer-readable medium described herein, the one or more parameters associated with the physical activity comprise a type of the physical activity, a duration of the activity segment, a distance traveled by the user during the activity segment, an elevation change of the user during the activity segment, a quantity of calories burned by the user during the activity segment, or any combination thereof.

In some examples of the method, apparatuses, and non-transitory computer-readable medium described herein, the one or more parameters associated with the physical activity comprise a pace, a speed, an elevation, a route map, a split time, an elevation-adjusted pace, or any combination thereof.

Some examples of the method, apparatuses, and non-transitory computer-readable medium described herein may further include operations, features, means, or instructions for identifying a first geographical position of the user at a start of the activity segment and a second geographical position of the user at an end of the activity segment, wherein identifying the one or more parameters associated with the physical activity may be based at least in part on the first geographical position, the second geographical position, or both.

Some examples of the method, apparatuses, and non-transitory computer-readable medium described herein may further include operations, features, means, or instructions for receiving, from a server, activity classification data associated with the activity segment, the activity classification data including a plurality of classified activity types and corresponding confidence values, the confidence values indicating a confidence level associated with the corresponding classified activity type, wherein identifying the one or more parameters associated with the physical activity may be based at least in part on receiving the activity classification data.

Some examples of the method, apparatuses, and non-transitory computer-readable medium described herein may further include operations, features, means, or instructions for causing the GUI of the user device to display one or more classified activity types of the plurality of classified activity types based at least in part on receiving the activity classification data and receiving, via the user device and in response to displaying the one or more classified activity types, a selection of a classified activity type of the one or more classified activity types, wherein identifying the one or more parameters associated with the physical activity may be based at least in part on receiving the selection.

In some examples of the method, apparatuses, and non-transitory computer-readable medium described herein, the physiological data includes temperature data, accelerometer data, heart rate data, respiratory rate data, or any combination thereof.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user using based on arterial blood flow.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can include RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for automatic activity detection, comprising:
   identifying, by one or more processors, one or more previous routes associated with one or more previous activity segments of a user;
   receiving, by the one or more processors, physiological data associated with the user from a wearable device;
   identifying, by the one or more processors based at least in part on the physiological data, an activity segment during which the user is engaged in a physical activity;
   identifying, by the one or more processors, location data associated with a route of the user for at least a portion of the activity segment, the location data comprising at least a starting location of the activity segment;
   automatically identifying, by the one or more processors without a user input, a completion of the activity segment based at least in part on identifying an end point of the activity segment along the route of the location data associated with the activity segment, wherein the end point of the activity segment is based at least in part on an ending location of the one or more previous routes associated with the one or more previous activity segments;
   identifying, by the one or more processors, one or more parameters associated with the physical activity based at least in part on the physiological data and the location data, and based at least in part on automatically identifying the completion of the activity segment; and
   transmitting a signal configured to cause a graphical user interface of a user device to display the one or more parameters associated with the physical activity.

2. The method of claim 1, further comprising:
   causing the graphical user interface of the user device to display an indication of the activity segment; and
   receiving, via the user device and in response to the indication of the activity segment, a confirmation of the activity segment, wherein causing the graphical user interface to display the one or more parameters associated with the physical activity is based at least in part on receiving the confirmation.

3. The method of claim 2, wherein the confirmation is received after a start of the identified activity segment, wherein identifying the one or more parameters associated with the physical activity comprises:
   identifying the one or more parameters associated with the physical activity based at least in part on physiological data and location data associated with a portion of the activity segment between the start of the activity segment and receipt of the confirmation.

4. The method of claim 1, further comprising:
identifying a plurality of candidate activity types associated with the activity segment based at least in part on the received physiological data; and
determining a plurality of confidence values associated with the plurality of candidate activity types based at least in part on the location data, wherein identifying the one or more parameters is based at least in part on the plurality of confidence values.

5. The method of claim 1, further comprising:
receiving, via the user device, a user input which selectively modifies at least one parameter of the one or more parameters associated with the physical activity.

6. The method of claim 1, wherein the one or more parameters associated with the physical activity comprise a type of the physical activity, a duration of the activity segment, a distance traveled by the user during the activity segment, an elevation change of the user during the activity segment, a quantity of calories burned by the user during the activity segment, or any combination thereof.

7. The method of claim 1, wherein the one or more parameters associated with the physical activity comprise a pace, a speed, an elevation, a route map of the route, a split time, an elevation-adjusted pace, or any combination thereof.

8. The method of claim 1, further comprising:
inputting, into a machine learning model, the location data, the physiological data, the one or more previous routes, previous physiological data associated with the one or more previous activity segments, or any combination thereof, wherein automatically identifying a completion of the activity segment is based at least in part on an output of the machine learning model.

9. The method of claim 1, further comprising:
receiving, from a server, activity classification data associated with the activity segment, the activity classification data including a plurality of classified activity types and corresponding confidence values, the confidence values indicating a confidence level associated with the corresponding classified activity type, wherein identifying the one or more parameters associated with the physical activity is based at least in part on receiving the activity classification data.

10. The method of claim 9, further comprising:
causing the graphical user interface of the user device to display one or more classified activity types of the plurality of classified activity types based at least in part on receiving the activity classification data; and
receiving, via the user device and in response to displaying the one or more classified activity types, a selection of a classified activity type of the one or more classified activity types, wherein identifying the one or more parameters associated with the physical activity is based at least in part on receiving the selection.

11. The method of claim 1, wherein the completion of the activity segment is automatically identified at a first time, the method further comprising:
receiving, via the user device at a second time that is subsequent to the first time, the user input confirming the completion of the activity segment, wherein the one or more parameters of the physical activity are identified based at least in part on the completion of the activity segment occurring at the first time.

12. The method of claim 1, wherein the wearable device comprises a wearable ring device.

13. The method of claim 1, wherein automatically identifying the completion of the activity segment is based at least in part on comparing the route of the activity segment to the one or more previous routes.

14. An apparatus for automatic activity detection, comprising:
one or more processors;
one or more memories coupled with the one or more processors; and
instructions stored in the one or more memories and executable by the one or more processors to cause the apparatus to:
identify one or more previous routes associated with one or more previous activity segments of a user;
receive physiological data associated with the user from a wearable device;
identify, based at least in part on the physiological data, an activity segment during which the user is engaged in a physical activity;
identify location data associated with a route of the user for at least a portion of the activity segment, the location data comprising at least a starting location of the activity segment;
automatically identify, without a user input, a completion of the activity segment based at least in part on identifying an end point of the activity segment along the route of the location data associated with the activity segment, wherein the end point of the activity segment is based at least in part on an ending location of the one or more previous routes associated with the one or more previous activity segments;
identify one or more parameters associated with the physical activity based at least in part on the physiological data and the location data, and based at least in part on automatically identifying the completion of the activity segment; and
transmit a signal configured to cause a graphical user interface of a user device to display the one or more parameters associated with the physical activity.

15. The apparatus of claim 14, wherein the instructions are further executable by the one or more processors to cause the apparatus to:
cause the graphical user interface of the user device to display an indication of the activity segment; and
receive, via the user device and in response to the indication of the activity segment, a confirmation of the activity segment, wherein causing the graphical user interface to display the one or more parameters associated with the physical activity is based at least in part on receiving the confirmation.

16. The apparatus of claim 15, wherein the instructions to identify the one or more parameters associated with the physical activity are executable by the one or more processors to cause the apparatus to:
identify the one or more parameters associated with the physical activity based at least in part on physiological data and location data associated with a portion of the activity segment between a start of the activity segment and receipt of the confirmation.

17. The apparatus of claim 14, wherein, to automatically identify the completion of the activity segment, the instructions are further executable by the one or more processors to cause the apparatus to:
automatically identify the completion of the activity segment based at least in part on the received physiological data.

18. The apparatus of claim 17, wherein the instructions are further executable by the one or more processors to cause the apparatus to:
   receive, via the user device, a user input which selectively modifies at least one parameter of the one or more parameters associated with the physical activity.

19. The apparatus of claim 14, wherein the one or more parameters associated with the physical activity comprise a type of the physical activity, a duration of the activity segment, a distance traveled by the user during the activity segment, an elevation change of the user during the activity segment, a quantity of calories burned by the user during the activity segment, or any combination thereof.

20. The apparatus of claim 14, wherein the one or more parameters associated with the physical activity comprise a pace, a speed, an elevation, a route map of the route, a split time, an elevation-adjusted pace, or any combination thereof.

* * * * *